(12) United States Patent
Sadeghzadeh et al.

(10) Patent No.: US 11,389,587 B2
(45) Date of Patent: Jul. 19, 2022

(54) PATIENT MONITORING SYSTEMS AND RELATED PRESENTATION METHODS

(71) Applicant: MEDTRONIC MINIMED, INC., Northridge, CA (US)

(72) Inventors: Mahta Sadeghzadeh, Los Angeles, CA (US); Catherine T. Fogel, Castaic, CA (US); Magnus Johansson, Oak Park, CA (US); Julia Steele Rodriguez, Burbank, CA (US); Shweta Gopalakrishnan, Woodland Hills, CA (US); Kristin Andreassen, Santa Monica, CA (US); Maxwell Koobatian, Oak Park, CA (US); Isaac Kidd, Sherman Oaks, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 218 days.

(21) Appl. No.: 16/269,545

(22) Filed: Feb. 6, 2019

(65) Prior Publication Data
US 2020/0246543 A1 Aug. 6, 2020

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ... A61B 5/14532; A61B 5/4839; A61B 5/743; A61B 5/7275; A61B 5/7435;
(Continued)

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

WO WO-2011126624 A1 * 10/2011 ............. G06Q 10/00

OTHER PUBLICATIONS

Buell, The Health Continuum: Leveraging IT Optimize Care, Jan./Feb. 2018, Healthcare Executive, pp. 10-18. (Year: 2018).*

(Continued)

*Primary Examiner* — Christopher L Gilligan
(74) *Attorney, Agent, or Firm* — Carter, DeLuca & Farrell LLP

(57) ABSTRACT

Medical devices and related patient management systems and methods are provided. A method of monitoring a plurality of patients involves a computing device obtaining measurement data for the plurality of patients from a database, obtaining one or more prioritization rules from the database, generating a prioritized list of the plurality of patients based on the measurement data in accordance with the one or more prioritization rules, and providing a dashboard graphical user interface (GUI) display including the prioritized list. The prioritized list on the dashboard GUI display is dynamically updated in accordance with the prioritization rule(s) in response to updated measurement data in the database.

17 Claims, 16 Drawing Sheets

(51) Int. Cl.
*A61B 5/00* (2006.01)
*G16H 20/17* (2018.01)
*G16H 10/60* (2018.01)
*G16H 15/00* (2018.01)
*G16H 70/40* (2018.01)

(52) U.S. Cl.
CPC ............ *G16H 10/60* (2018.01); *G16H 20/17* (2018.01); *A61B 5/7275* (2013.01); *A61B 5/743* (2013.01); *G16H 15/00* (2018.01); *G16H 70/40* (2018.01)

(58) Field of Classification Search
CPC .... A61B 5/0022; A61B 5/0004; G16H 20/17; G16H 10/60; G16H 15/00; G16H 70/40; G16H 40/20; A61M 2205/3553; A61M 2205/502; A61M 2205/505
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2006/0031094 A1 | 2/2006 | Cohen et al. |
| 2007/0123819 A1 | 5/2007 | Mernoe et al. |
| 2010/0160861 A1 | 6/2010 | Causey, III et al. |
| 2013/0325352 A1* | 12/2013 | Greene ................ G16H 40/63 702/19 |
| 2013/0338630 A1 | 12/2013 | Agrawal et al. |
| 2015/0113422 A1* | 4/2015 | Pfeiffer ................ G16H 10/60 715/739 |
| 2017/0061093 A1* | 3/2017 | Amarasingham ..... G06F 19/325 |
| 2017/0169175 A1* | 6/2017 | Graff ..................... G16H 10/60 |
| 2017/0308662 A1* | 10/2017 | Hamilton ............... G16H 40/67 |
| 2018/0153478 A1* | 6/2018 | Johnson ............. A61B 5/14542 |
| 2018/0226150 A1* | 8/2018 | Hayter ................. G16H 40/63 |
| 2020/0204631 A1* | 6/2020 | Subramaniam ....... H04L 67/141 |

OTHER PUBLICATIONS

Fletcher, Effect of a Real-Time Electronic Dashboard on a Rapid Response System, Nov. 20, 2017, Journal of Medical Systems, pp. 1-10. (Year: 2017).*

* cited by examiner

FIG. 2

Dr. Sara Smith

06/06/2018

Patient List

[+ Add New Patient]  [+ Add New Settings]  [💾 SAVE UPDATES]

Show [8 ▼] entries

| Photo ▼ | Patient ID ▼ | Name ▼ | Status ▼ | Reason ▼ | Action | Latest Notes on Patient |
|---|---|---|---|---|---|---|
| 👤 | 96095 | Kevin Adams | 72% | ↓ Δ10%TIR | ☎ 💬 ✉ ⇧ | Inc in TIR, adj ACT from 4 hrs. to 3.5 hrs. |
| 👤 | 17522 | Tom Smith | 79% | Therapy Setting: ACT ↑ 3.5 hrs. | ☎ 💬 ✉ ⇧ | No change, pt. doing well! |
| 👤 | 19940 | Rachel Lu | 80% | N/A | ☎ 💬 ✉ ⇧ | Newly diagnosed T1 pt. |
| 👤 | 28050 | David Dodge | 93% | N/A | ☎ 💬 ✉ ⇧ | T2 pt with increase insulin needs |
| 👤 | 66698 | Mayo Swig | 82% | N/A | ☎ 💬 ✉ ⇧ | Post meal lows, call with nutrients |
| 👤 | 95155 | Chris Jackson | 85% | N/A | ☎ 💬 ✉ ⇧ | Test msg to encourage good compliance |
| 👤 | 68710 | Julie Yellen | 87% | N/A | ☎ 💬 ✉ ⇧ | Data reviewed on 6/10, no change |
| 👤 | 19666 | Bob Evans | 83% | N/A | ☎ 💬 ✉ ⇧ | New to pump therapy, Settings being adjusted |

PATIENT MONITORING SYSTEMS AND RELATED PRESENTATION METHODS

TECHNICAL FIELD

Embodiments of the subject matter described herein relate generally to medical devices and related patient monitoring systems, and more particularly, embodiments of the subject matter relate to patient monitoring systems providing automatically prioritized patient lists.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Managing a diabetic's blood glucose level is complicated by variations in a user's daily activities (e.g., exercise, carbohydrate consumption, and the like) in addition to variations in the user's individual insulin response and potentially other factors. Physicians have recognized that continuous monitoring provides a greater understanding of a patient's glycemic profile, and accordingly, continuous glucose monitoring (CGM) has recently been employed to gain insight into a patient's condition and make appropriate therapy and lifestyle recommendations to achieve improved glucose control.

In practice, physicians or other healthcare providers may devote time and resources on patients who are asymptomatic or who otherwise do not require therapy or lifestyle modifications, for example, during routine or regularly scheduled appointments. Often, such time and resources could be better spent on patients who are more symptomatic or otherwise require higher maintenance. However, physicians and other healthcare providers lack insight into which patients are or are not symptomatic or who may otherwise benefit from intervention at any point in time. Accordingly, there is a need improve awareness of symptomatic patients to facilitate improved outcomes and improve efficiency while minimizing the burdens physicians or other healthcare providers.

BRIEF SUMMARY

Medical devices and related systems and operating methods are provided. An embodiment of a method of monitoring a plurality of patients involves a computing device obtaining measurement data for the plurality of patients from a database, obtaining one or more prioritization rules from the database, generating a prioritized list of the plurality of patients based on the measurement data in accordance with the one or more prioritization rules, and providing a dashboard graphical user interface (GUI) display including the prioritized list. In exemplary embodiments, the method continues by dynamically updating the prioritized list in response to updated measurement data in the database, resulting in an updated prioritized list of the plurality of patients, wherein the dashboard GUI display is dynamically updated to reflect the updated prioritized list.

In another embodiment, a system is provided that includes a display device having rendered thereon a patient monitoring dashboard graphical user interface (GUI) display for concurrently monitoring a plurality of patients. The patient monitoring dashboard GUI display includes a patient list region having a patient identification column, a patient status column, and a plurality of rows corresponding to the plurality of patients. Each row of the plurality of rows is associated with a respective patient of the plurality of patients and includes a graphical representation of respective identification information associated with the respective patient in the patient identification column of the respective row and a graphical representation of a current status of a physiological condition of the respective patient in the patient status column of the respective row. For each row of the plurality of rows, the current status of the physiological condition of the respective patient in the patient status column of the respective row is determined based at least in part on respective measurement data associated with the respective patient obtained from a database, and each row of the plurality of rows is ordered within the patient list region based at least in part on the current status of the physiological condition of the respective patient in accordance with one or more prioritization rules.

In another embodiment, a system includes a database and a computing device coupled to the database. The database maintains one or more prioritization rules along with maintain measurement data for a physiological condition of a plurality of patients, wherein respective measurement data associated with a respective patient of the plurality of patients is obtained from a respective medical device associated with the respective patient. The computing device obtains the measurement data for the plurality of patients from the database, obtains the one or more prioritization rules from the database, generates a prioritized list of the plurality of patients based on the measurement data in accordance with the one or more prioritization rules, and provides a patient monitoring dashboard graphical user interface (GUI) display including a graphical representation of the prioritized list.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

FIGS. 2-4 depict exemplary embodiments of patient monitoring dashboard graphical user interface (GUI) displays that may be presented on a display device associated with a computing device in one or more embodiments;

DETAILED DESCRIPTION

Figure 1:
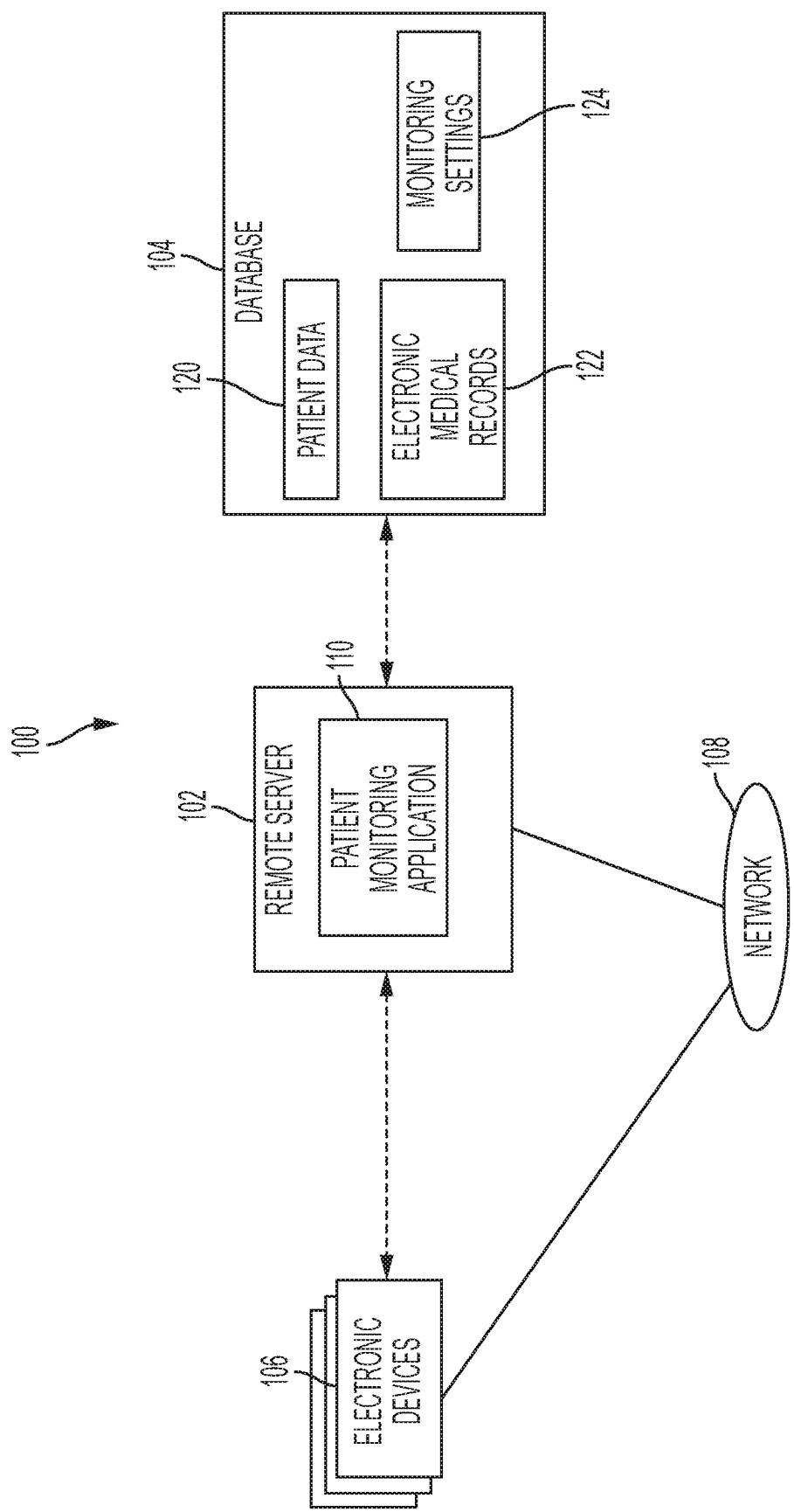
FIG. 1 depicts an exemplary embodiment of a patient data management system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter may be implemented in an equivalent manner in the context of other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. That said, the subject matter described herein can be utilized more generally in the context of overall diabetes management or other physiological conditions independent of or without the use of an infusion device or other medical device (e.g., when oral medication is utilized), and the subject matter described herein is not limited to any particular type of medication.

Generally, a fluid infusion device includes a motor or other actuation arrangement that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments of the subject matter described herein generally relate to systems for presenting information pertaining to the real-time physiological condition of multiple patients concurrently for monitoring by a physician or other healthcare provider. operation of the infusion device delivering fluid to a body of a user. In exemplary embodiments, a dashboard graphical user interface (GUI) is presented on an electronic device, and the dashboard GUI display includes or otherwise provides a listing of patients with graphical representations or other graphical indicia of various aspects of the physiological condition of each respective patient. For example, the dashboard GUI display may include graphical representations of a diabetic patient's glucose level or one or more other metric(s) indicative of or correlative to the patient's glucose level, along with other indicia pertaining to the patient's physiological condition.

In exemplary embodiments, the listing of patients on the dashboard GUI display is prioritized in accordance with one or more prioritization rules and dynamically updated in real-time in response to changes to the physiological condition to one or more patients. In this regard, infusion devices, continuous glucose monitoring (CGM) devices, or other medical devices associated with the patients may periodically or continually obtain new measurements of a respective patient's glucose level and upload the measurement data to a remote server or database substantially in real-time. As the glycemic state of different patients change, they move up or down in the prioritized list according to the prioritization rules. In this regard, symptomatic patients or patients experiencing adverse events may be ordered or prioritized towards the top of the list on the dashboard GUI display, while patients who are not symptomatic or are otherwise exhibiting normal glycemic levels may be deprioritized below those patients who are more likely to be in need of attention or intervention.

FIG. 1 depicts an exemplary embodiment of a patient data management system 100 that includes, without limitation, a computing device 102 coupled to a database 104 that is also communicatively coupled to one or more electronic devices 106 over a communications network 108, such as, for example, the Internet, a cellular network, a wide area network (WAN), or the like. It should be appreciated that FIG. 1 depicts a simplified representation of a patient data management system 100 for purposes of explanation and is not intended to limit the subject matter described herein in any way.

In exemplary embodiments, the electronic devices 106 include one or more medical devices, such as, for example, an infusion device, a sensing device, a monitoring device, a CGM device, and/or the like. Additionally, the electronic devices 106 may include any number of non-medical client electronic devices, such as, for example, a mobile phone, a smartphone, a tablet computer, a smart watch, or other similar mobile electronic device, or any sort of electronic device capable of communicating with the computing device 102 via the network 108, such as a laptop or notebook computer, a desktop computer, or the like. One or more of the electronic devices 106 may include or be coupled to a display device, such as a monitor, screen, or another conventional electronic display, capable of graphically presenting data and/or information pertaining to the physiological condition of a patient. Additionally, one or more of the electronic devices 106 also includes or is otherwise associated with a user input device, such as a keyboard, a mouse, a touchscreen, a microphone, or the like, capable of receiving input data and/or other information from a user of the electronic device 106.

In exemplary embodiments, one or more of the electronic devices 106 transmits, uploads, or otherwise provides data or information to the computing device 102 for processing at the computing device 102 and/or storage in the database 104. For example, when an electronic device 106 is realized as a sensing device, monitoring device, or other device that includes sensing element is inserted into the body of a patient or otherwise worn by the patient to obtain measurement data indicative of a physiological condition in the body of the patient, the electronic device 106 may periodically upload or otherwise transmit the measurement data to the computing device 102. In other embodiments, the measurement data from a sensing device 106 may be provided to an infusion device or another intermediary device 106, which, in turn periodically uploads or transmits the measurement data to the computing device 102. When the electronic device 106 is realized as an infusion device or similar device capable of delivering a fluid or medicament to a patient, the electronic device 106 may also periodically upload or otherwise transmit delivery data indicating the timing and amounts of the fluid or medicament being delivered to the patient. In yet other embodiments, client electronic device 106 may be utilized by a patient to manually define, input or otherwise log meals, activities, or other events experienced by the patient and then transmit, upload, or otherwise provide such event log data to the computing device 102.

The computing device 102 generally represents a server or other remote device configured to receive data or other information from the electronic devices 106, store or otherwise manage data in the database 104, and analyze or otherwise monitor measurement data received from the electronic devices 106 and/or stored in the database 104 and provide a patient monitoring dashboard GUI display, as described in greater detail below. In practice, the computing device 102 may reside at a location that is physically distinct and/or separate from the electronic devices 106, such as, for example, at a facility that is owned and/or operated by or otherwise affiliated with a manufacturer of one or more medical devices utilized in connection with the patient data management system 100. For purposes of explanation, but without limitation, the computing device 102 may alternatively be referred to herein as a server, a remote server, or variants thereof. The server 102 generally includes a processing system and a data storage element (or memory) capable of storing programming instructions for execution by the processing system, that, when read and executed, cause processing system to create, generate, or otherwise facilitate the applications or software modules configured to perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In exemplary embodiments, the database 104 is utilized to store or otherwise maintain historical observational patient data 120 (e.g., measurement data, event log data, and the like) and electronic medical records data 122 for a plurality of different patients. In this regard, a subset of patients having associated data in one of the data sets 120, 122, may also have associated data in another one of the data sets 120, 122. That is, some but not necessarily all of the patients having associated with one of the data sets 120, 122 may be common to another of the data sets 120, 122. In exemplary embodiments, the database 104 also stores or maintains monitoring settings data 124 utilized to analyze or monitor the data 120, 122 maintained in the database 104 and generate GUI displays or initiate other actions based on the data 120, 122, as described in greater detail below. In this regard, the setting data 124 may include prioritization rules or other thresholds, criteria or logic for ordering or prioritizing the presentation of patients on a dashboard GUI display and/or initiating actions substantially in real-time in response to updated patient measurement data 120 in the database 104, as described in greater detail below.

In the illustrated embodiment, the server 102 implements or otherwise executes a patient monitoring application 110 that receives or otherwise obtains patient data 120, 122 and monitoring settings data 124 from the database 104 and generates or otherwise provides a dashboard GUI display using the patient data 120, 122 in accordance with the monitoring settings data 124. The dashboard GUI display may be presented at the server 102 or provided by the server 102 to another electronic device 106 via the network 108 for presentation at the electronic device 106.

Still referring to FIG. 1, in exemplary embodiments, the historical observational data 120 maintained in the database 104 includes, in association with a particular patient (or patient identifier), one or more of: historical measurement data indicative of the patient's physiological condition (e.g., historical blood glucose values, historical interstitial glucose values, and/or the like) with respect to time, historical delivery data indicative of dosages of fluid or medicament delivered to the patient (e.g., historical meal or correction boluses, basal dosages or other automated delivery amounts, and the like) with respect to time, historical meal data and/or other event log data associated with the patient, historical contextual data pertaining to the measurement data, the delivery data, the event log data, and the like. For example, the server 102 may receive, from a medical device via the network 108, measurement data values associated with a particular patient (e.g., sensor glucose measurements, acceleration measurements, and the like) that were obtained using a sensing element, and the server 102 stores or otherwise maintains the historical measurement data as patient data 120 in the database 104 in association with the patient (e.g., using one or more unique patient identifiers). Additionally, the server 102 may also receive, from or via a client device 106, meal data or other event log data that may be input or otherwise provided by the patient (e.g., via a client application at the client device 106) and store or otherwise maintain historical meal data and other historical event or activity data associated with the patient in the database 104. In this regard, the meal data include, for example, a time or timestamp associated with a particular meal event, a meal type or other information indicative of the content or nutritional characteristics of the meal, and an indication of the size associated with the meal. In exemplary embodiments, the server 102 also receives historical fluid delivery data (e.g., insulin delivery dosage amounts and corresponding timestamps) corresponding to basal or bolus dosages of fluid delivered to the patient by an infusion device 106. The server 102 may also receive geolocation data and potentially other contextual data associated with an electronic device 106 providing the patient data 120, and store or otherwise maintain the historical operational context data in association with the particular patient. In this regard, one or more of the devices 106 may include a global positioning system (GPS) receiver or similar modules, components or circuitry capable of outputting or otherwise providing data characterizing the geographic location of the respective device 106 in real-time.

The electronic medical records (EMR) data 122 generally includes, in association with one or more identifiers for a given patient within the EMR data set, information indicative of medical diagnoses or medical conditions the patient has been diagnosed with, drugs or medications that have been administered or taken by the patient, prescription information, therapy changes for the patient, laboratory results or measurements for physiological conditions of the patient, immunization records for the patient, microbiology results or other observations pertaining to the patient, healthcare utilization information (e.g., hospitalizations, emergency room visits, outpatient visits, etc.), x demographic information associated with the patient (e.g., age, income, education, location, gender), past medical procedures, clinical observations or other habitual behavior information (e.g., smoking, alcohol usage, etc.), family medical history, physician notes and care plans, and/or the like. The EMR data 122 may also include data about the healthcare provider(s) associated with various aspects of a patient's medical records, the patient's insurance information, and/or the like. In various embodiments, the EMR data 122 could be received or obtained by the server 102 from another server computing device, another database different from database 104 (e.g., by replication from another database), individual computing devices associated with healthcare providers, patients, and/or the like.

FIG. 2 depicts an exemplary embodiment of a patient monitoring dashboard GUI display 200 that may be presented on a display device associated with an electronic device, such as, for example, a computing device, a portable medical device, a sensor device, or the like. In one or more exemplary embodiments, data, code, or other information for generating the patient monitoring dashboard GUI display 200 is provided by the remote server 102 to a computing device 106 that is communicatively coupled to the server 102 over the network 108. The dashboard GUI display 200 is a tabbed GUI display that includes a patient list tab 202 that is selectable to present a patient list region 204 below the patient list tab 202. The patient list region 204 includes a listing of patients associated with the doctor or other healthcare provider utilizing the electronic device viewing the dashboard GUI display 200. In this regard, in one or more embodiments, the patient list tab 202 is selected or otherwise activated by default, with the patient list region 204 being populated with a listing of patients associated with the user of the electronic device in response to authenticating the user of the electronic device (e.g., upon a doctor or other healthcare provider logging in to the patient monitoring application 110 provided by the server 102). As described in greater detail below, in exemplary embodiments, the listing of patients presented within the patient list region 204 is prioritized or otherwise ordered in accordance with one or more prioritization rules associated with the particular doctor or healthcare provider.

In exemplary embodiments, the patient list region 204 includes a number of horizontal rows, where each row is associated with an individual patient associated with the doctor or healthcare provider viewing the patient monitoring dashboard GUI display 200. The illustrated patient monitoring dashboard GUI display 200 includes a drop-down menu 203 or similar GUI element that may be manipulated by a user to control or otherwise configure the number of patients to be depicted in the patient list region 204. The patient list region 204 also includes a number of vertical columns corresponding to different fields of data or information associated with the patients presented in the patient list region 204. In the illustrated embodiment, the patient list region 204 includes a first column 210 for a patient photograph, a second column 212 for a patient identification number, and a third column 214 for the patient name.

A patient status column 216 corresponds to a metric indicative of a physiological condition of the displayed patients. In exemplary embodiments, the remote server 102 and/or the monitoring application 110 calculates or otherwise determines, for each patient, a respective value for the metric substantially in real-time based on the most recently available measurement data associated with the respective patient. For example, in the illustrated embodiment, the patient status column 216 corresponds to a time in range metric, where the remote server 102 and/or the monitoring application 110 calculates or otherwise determines, for each patient, a percentage of preceding monitoring time period during which the patient's measured glucose was within a target range of values above a lower glucose threshold but below an upper glucose threshold. In this regard, the time in range percentage may be graphically indicated using a progress bar, status bar, or similar GUI element where a ratio of a filled portion of the GUI element to an unfilled portion of the GUI elements corresponds to the time in range percentage. It should be noted that the upper and lower glucose values defining the target glucose range may vary from one patient to another, that is, the time in range metric values may be determined for each patient using patient-specific target range thresholds, which may be stored or otherwise maintained in association with the patient in the database 104. In response to a new or updated glucose measurement value for a patient being pushed or otherwise provided to the database 104, the remote server 102 and/or the monitoring application 110 may dynamically update that patient's time in range value in real-time to reflect the patient's most recently obtained glucose measurement.

In the illustrated embodiment of FIG. 2, another column 218 adjacent to the patient status column 216 corresponds to notifications or other graphical indicia pertaining to the patient's current physiological condition. As described in greater detail below in the context of FIGS. 3-4, in exemplary embodiments, the listing of patients in the patient region 204 are prioritized or otherwise ordered in accordance with one or more prioritization rules, where the column 218 may utilized to provide a notification pertaining to the patient's physiological condition or other indication of the underlying reason that dictated or otherwise influenced the respective patient's ranking in the list.

Still referring to FIG. 2, exemplary embodiments of the patient monitoring dashboard GUI display 200 include an action column 220 that includes GUI elements 222, 224, 226, 228 that are selectable to initiate or otherwise perform an action with respect to a particular patient. For example, in the illustrated embodiment, the action column 220 includes a phone call button 222 for initiating a phone call with the patient associated with a particular row in the patient list region 204 (e.g., using a phone number stored in the database 104 in association with the patient), a text message button 224 to initiate sending a text message to the respective patient, an email button 226 to initiate sending an email to the respective patient, and a report button 228 to initiate presentation of a report associated with the respective patient. Additionally, the illustrated patient monitoring dashboard GUI display 200 includes a patient notes column 230 that includes the most recent physician notes associated with a respective patient that are obtained from the electronic medical records data 122 maintained in the database 104.

Figure 3:
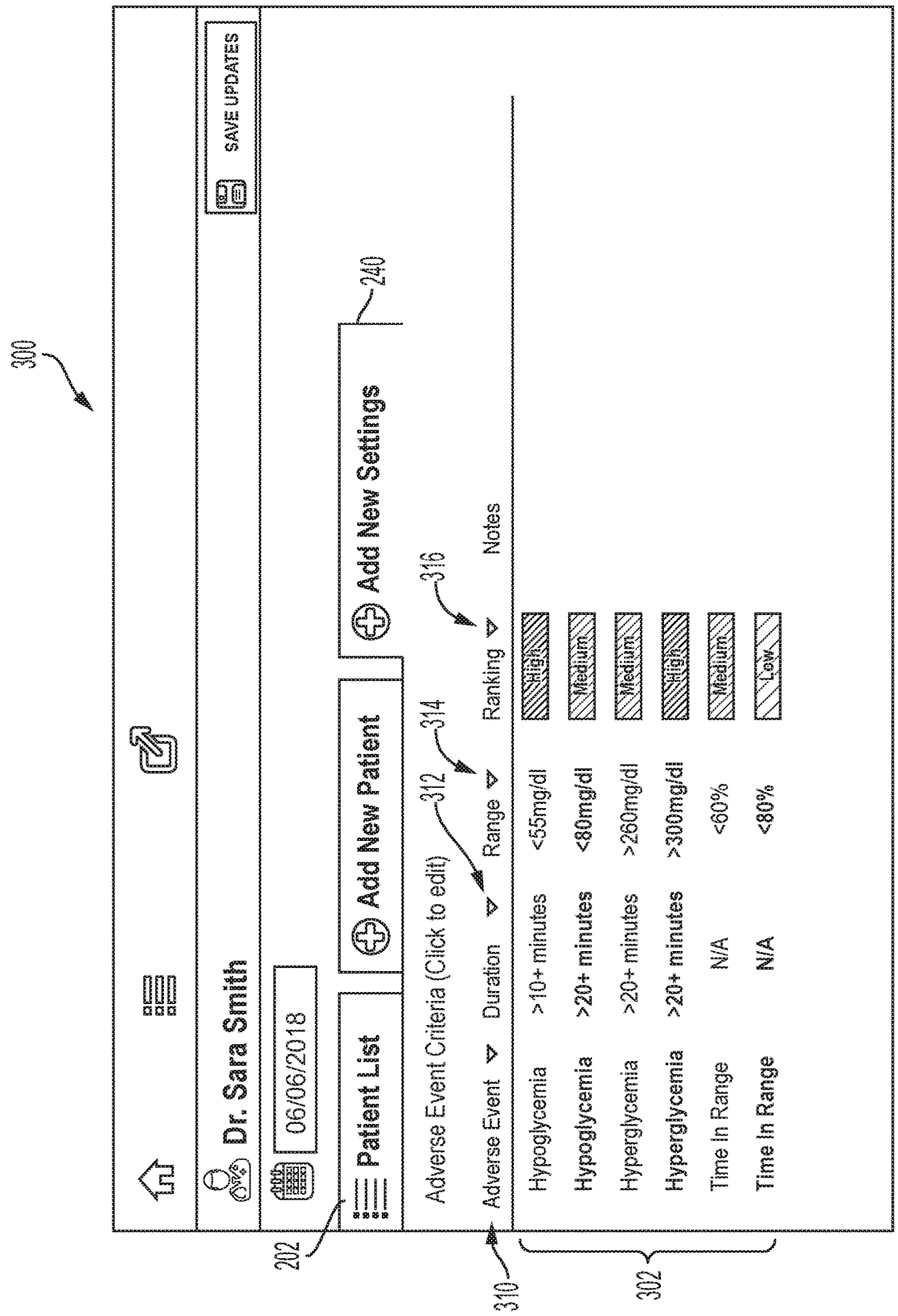

Referring now to FIG. 3 with continued reference to FIGS. 1-2, in response to selection of a patient monitoring settings tab 240, an updated patient monitoring dashboard GUI display 300 may be generated or otherwise provided that includes a region 302 that lists prioritization criteria that have been created or otherwise defined for ordering patients in the patient list region 204. In this regard, the vertical columns 310, 312, 314, 316 across the prioritization rules region 302 define the fields or parameters for the respective prioritization rules or criteria to be applied when generating the patient list region 304. In exemplary embodiments, a first column 310 is utilized to define a type of adverse event to be utilized for prioritization, a second column 312 is utilized to define a duration of the adverse event to be utilized for prioritization, a third column 314 is utilized to define a measurement value for the adverse event, and a fourth column 316 is utilized to assign a ranking or priority to the respective adverse event being utilized for prioritization. In this regard, patients exhibiting adverse events assigned higher levels of priority may be ordered in the patient list region 204 ahead of other patients that are asymptomatic or exhibiting adverse events assigned relatively lower levels of priority. In situations where multiple patients may be exhibiting multiple different prioritizable adverse events concurrently, the subset of patients exhibiting the highest priority events may be ordered first, with those patients being ordered within that respective subset being ordered in accordance with their relative number or severity of adverse events, with the subset of patients exhibiting medium priority events being ordered after the highest priority subset, with those patients being ordered within that respective subset being ordered in accordance with their relative number or severity of adverse events, and so on.

The prioritization rules region 302 in FIG. 3 depicts prioritization rules for assigning the highest level of priority to patients exhibiting a hypoglycemic event with a measured glucose level below 55 mg/dL for more than 10 minutes or a hyperglycemic event with a measured glucose level above 300 mg/dL for more than 20 minutes. The prioritization rules depicted in FIG. 3 also assign a medium level of priority to patients exhibiting a hypoglycemic event with a measured glucose level below 80 mg/dL for more than 20 minutes, a hyperglycemic event with a measured glucose level above 260 mg/dL for more than 20 minutes, or a time in range percentage of less than 60%. Lastly, the lowest level or priority may be assigned to patients exhibiting a time in range of less than 80%. It should be appreciated that FIG. 3 is merely one exemplary set of prioritization rules for purposes of explanation, and the subject matter described herein is not intended to be limited to any particular type or number of prioritization rules or any particular scheme or manner for prioritizing patients. In this regard, any number of different prioritization rules or schemes may be utilized.

Additionally, although not illustrated in FIG. 3, in some embodiments, prioritization rules region 302 may also include additional columns for defining automated actions to be performed in response to detecting certain types of adverse events. In this regard, for each adverse event defined by the user for prioritization, the user may also define one or more notification rules that may be stored in association with the prioritization rules in the monitoring settings data 124 in the database 104, which, in turn, may be utilized to automatically provide notifications on behalf of the user to the particular patient exhibiting the adverse event. For example, user may specify that the patient should automatically receive a text message, an email, a push notification, or the like in response to detecting a particular adverse event. The body or content of the automated communication may also be configured or otherwise defined by the user. For example, a doctor or other healthcare provider may create a template message requesting the patient schedule an appointment or perform some other action, when the time in range falls below 60% and then create a notification rule associated with the time in range below 60% adverse event that results in the remote server 102 and/or the monitoring application 110 automatically initiating the desired type of communication with the autopopulated content to a particular patient in real-time in response to that patient's time in range falling below 60%. In this regard, automated notifications may be configured by the doctor or other healthcare provider to reduce the amount of time he or she spends on otherwise routine communications, thereby allowing the doctor or other healthcare provider to maintain focus on monitoring or assessing patients.

Referring again to FIG. 2 with reference to FIG. 3, when generating the patient list region 204, the server 102 and/or the monitoring application 110 analyzes the measurement data 120 associated with the user's associated patients to identify whether any of those patients are exhibiting a prioritizable adverse event, and then prioritizes those identified patients according to the relative priorities assigned to those adverse events. In this regard, the server 102 and/or the monitoring application 110 identifies patients Kevin Adams and Tom Smith as exhibiting the low priority adverse event of a time in range value below 80%. Accordingly, the initial rows of the patient list region 204 are populated with the data or information associated with Kevin Adams and Tom Smith, followed by the remaining patients that are asymptomatic or otherwise not exhibiting an adverse event. In the illustrated embodiment, the prioritized patients are ordered in ascending order according to their respective time in range values in the status column 216. Additionally, in exemplary embodiments, the graphical indicia 217, 219 in the status column 216 for Kevin Adams and Tom Smith may be rendered using a visually distinguishable characteristic (e.g., a yellow color) to indicate that they have a low priority adverse event associated therewith, while the status indicia for the remaining patients may be rendered with another visually distinguishable characteristic (e.g., a green color) to indicate they are asymptomatic or not exhibiting any prioritizable adverse events. The prioritization reason column 218 may also be populated with information that summarizes or otherwise characterizes their respective statuses or the reasons that each respective patient is prioritized above other patients.

For example, for patient Kevin Adams, the server 102 and/or the monitoring application 110 may calculate or otherwise determine that his time in range value has decreased by more than 10% since the user most recently viewed the patient monitoring GUI display 200 and provide indication of the drop in Kevin Adam's time in range as the reason Kevin Adams has been prioritized in the patient list region 204. Based on the information depicted in the status, reason, and notes columns 216, 218, 230 associated with Kevin Adams, a doctor or other healthcare provider may determine an action to be performed with respect to Kevin Adams and select the appropriate GUI element 222, 224, 226, 228 in the action column 220. For example, the user may select the email button 226 to open an email editor that may be utilized to compose an email to Kevin Adams to suggest potential therapy modifications, schedule an appointment, or the like.

It should be noted that in various embodiments, the headers associated with one or more columns 210, 212, 214, 216, 218, 230 may be selectable to re-sort or otherwise re-order the listing of patients and override the automated prioritization of the patient list region 204. For example, selecting the header for the status column 216 may result in the patient list region 204 being re-ordered in ascending or descending order according to the time in range metric values independently of any adverse events that may have been detected with respect to one or more of the patients.

Figure 4:
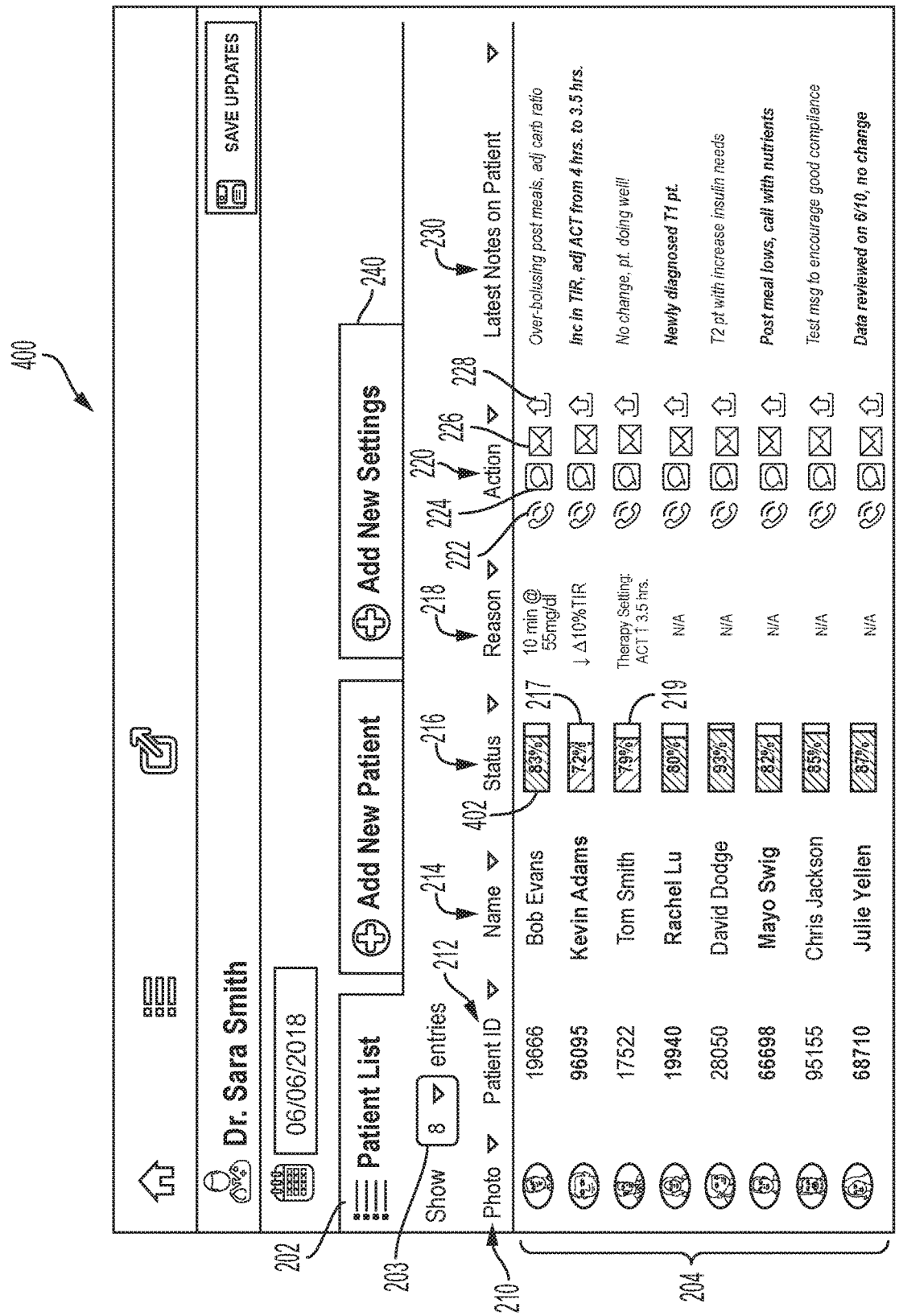

Referring to FIG. 4 with continued reference to FIGS. 1-3, in exemplary embodiments, the patient monitoring GUI display 200 is dynamically updated substantially in real-time in response to new or updated data being uploaded to the database 104 from the individual medical devices associated with the doctor's various patients. In this regard, FIG. 4 depicts an example where in response to updated glucose measurement data for patient Bob Evans, the server 102 and/or the monitoring application 110 determines the glucose measurements for Bob Evans have been below 55 mg/dL for greater than 10 minutes, and therefore, that Bob Evans is exhibiting a high priority hypoglycemic event. In response, the server 102 and/or the monitoring application 110 reorders or otherwise reprioritizes the patient list region 204 to rank or order Bob Evans ahead of patients exhibiting lower priority events, which, in turn, are ranked ahead of asymptomatic patients. The status indicia 402 associated with Bob Evans may also be rendered using a visually distinguishable characteristic (e.g., a red color) to indicate that a high priority adverse event, with indication of the type of adverse event depicted in the reason column 218 of the row associated with Bob Evans. A doctor or healthcare provider reviewing patients using the patient monitoring GUI display 200 may readily identify that patient Bob Evans may be in need of more immediate attention or intervention relative to other patients to mitigate the hypoglycemic event and select one of the phone call or text message GUI elements 222, 224 and attempt to expeditiously establish communications with Bob Evans to mitigate the hypoglycemic event before moving on to other patients who are currently less symptomatic.

Figure 5:
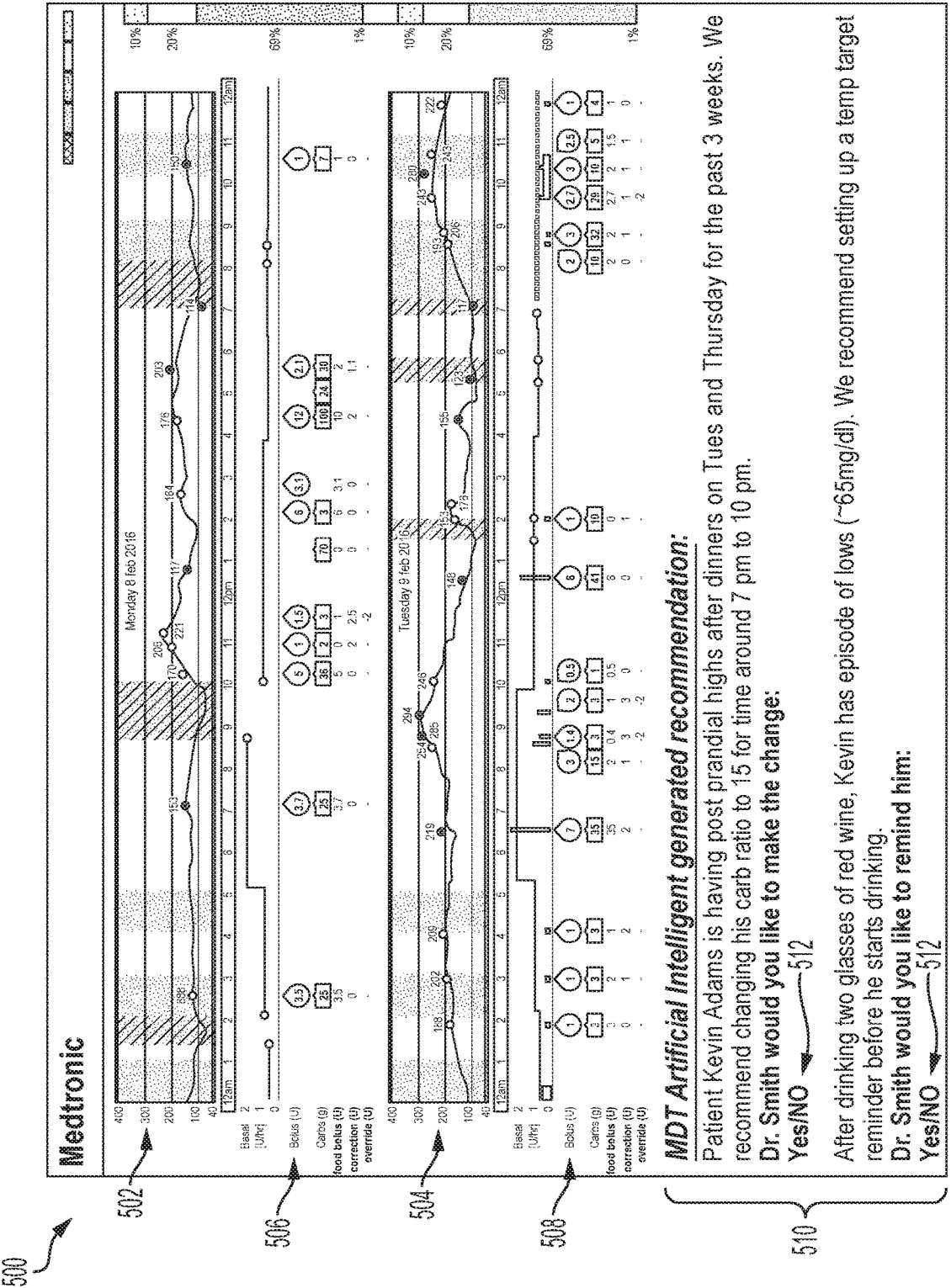
FIG. 5 depicts an exemplary embodiment of a report GUI display that may be presented on a display device associated with a computing device in one or more embodiments.

FIG. 5 depicts an exemplary report GUI display 500 that may be generated or otherwise provided by the server 102 and/or the monitoring application 110 in response to selection of the report GUI element 228 associated with patient Kevin Adams. In this regard, in response to the user selecting the report button 228 for Kevin Adams, the server 102 and/or the monitoring application 110 may query the database 104 for the historical measurement data, historical event log data, and/or other historical observational data 120 associated with Kevin Adams and then generate the report GUI display 500 that includes graph regions 502, 504 depicting graphical representations of the recent glucose measurement data for Kevin Adams with respect to time along with marker regions 506, 508 that include markers or other indicia associated with meals, boluses, or other events from the event log data associated with Kevin Adams at the appropriate times relative to the glucose measurement data. In exemplary embodiments, the report GUI display 500 includes a recommendation region 510 that depicts recommended therapeutic modifications for Kevin Adams that may be automatically determined by the server 102 and/or the monitoring application 110 based on the historical data 120 associated with Kevin Adams using artificial intelligence, machine learning, and/or the like. In one or more embodiments, the recommendation region 510 includes selectable GUI elements 512 that may be selected or otherwise manipulated to perform actions to facilitate the recommendations. For example, selection of a GUI element 512 may cause the server 102 and/or the monitoring application 110 to automatically generate a text message, push notification, or the like that transmits or otherwise provides information pertaining to the recommended action to a device associated with Kevin Adams, thereby allowing the doctor or healthcare provider to provide recommended actions to the patient substantially in real-time in an automated manner that reduces the burden on the doctor or healthcare provider.

Figure 6:
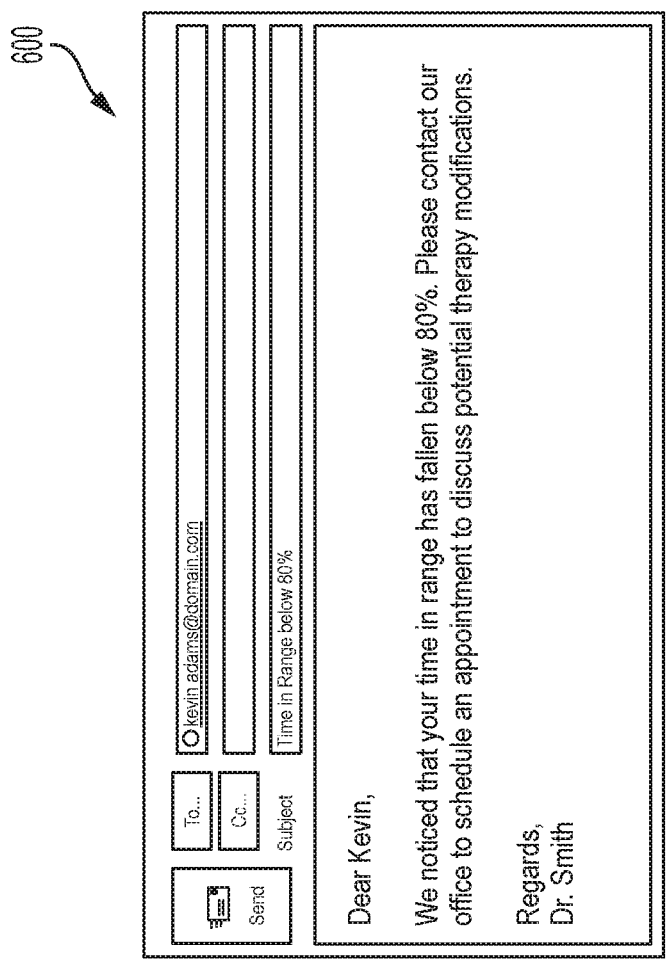
FIG. 6 depicts an exemplary embodiment of an email editor GUI display that may be presented on a display device associated with a computing device in one or more embodiments.

FIG. 6 depicts an exemplary embodiment of an email editor GUI display 600 that may be generated or otherwise provided by the server 102 and/or the monitoring application 110 in response to selection of the email GUI element 226 associated with patient Kevin Adams. In this regard, the server 102 and/or the monitoring application 110 may autopopulate the To: field of the email with a stored email address associated with Kevin Adams that is maintained in the database 104, and the Subject: field may be autopopulated with text that characterizes the adverse event that triggered the doctor or healthcare provider contacting the patient. Additionally, the server 102 and/or the monitoring application 110 may autopopulate the body of the email with a default template message, thereby allowing the doctor or healthcare provider to simply send the email without devoting any further time to editing or drafting the message. In this regard, in some embodiments, the template messages or subject used to autopopulate the email may be configurable or otherwise defined by the doctor or healthcare provider, thereby allowing the server 102 and/or the monitoring application 110 to autopopulate the email in the desired manner.

In a similar manner, the server 102 and/or the monitoring application 110 may automatically generate the text messages to be transmitted in response to selecting the text message button 224. For example, referring to FIG. 4, in response to selecting the text message button 224 associated with Bob Evans, the server 102 and/or the monitoring application 110 may automatically generate a text message configured to notify Bob Evans that he is currently experiencing a hypoglycemic event and should consume rescue carbohydrates or take other action, and the server 102 and/or the monitoring application 110 may automatically configure the text message to be sent to a stored phone number associated with Bob Evans in the database 104. The doctor or healthcare provider may then briefly review the text message and modify it as desired before sending it to the patient. That said, as described above, in other embodiments, notification rules may be created in conjunction with the prioritization rules to automatically generate messages or notifications to be provided to a symptomatic patient without requiring action by the doctor or healthcare provider, thereby allowing the doctor or healthcare provider to forego routine communications and continue analyzing or assessing the symptomatic patient's condition.

Figure 7:
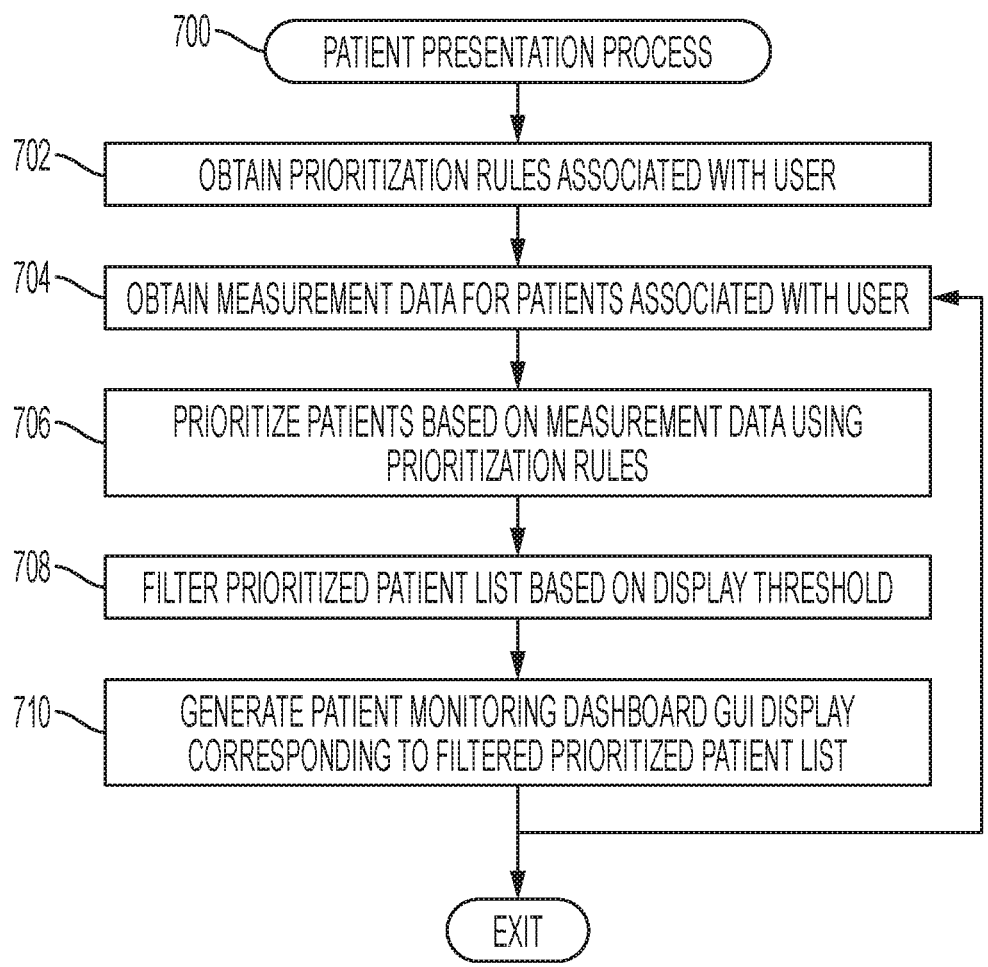
FIG. 7 is a flow diagram of an exemplary patient presentation process suitable for use with the patient data management system of FIG. 1 to generate a patient monitoring dashboard GUI display in one or more exemplary embodiments.

FIG. 7 depicts an exemplary patient presentation process 700 suitable for implementation by a patient management system to provide a patient monitoring dashboard GUI display. The various tasks performed in connection with the patient presentation process 700 may be performed by hardware, firmware, software executed by processing circuitry, or any combination thereof. For illustrative purposes, the following description refers to elements mentioned above in connection with FIG. 1. In practice, portions of the patient presentation process 700 may be performed by different elements of the patient management system 100, such as, for example, the server 102, the database 104, the client devices 106 and/or the patient monitoring application 110. It should be appreciated that the patient presentation process 700 may include any number of additional or alternative tasks, the tasks need not be performed in the illustrated order and/or the tasks may be performed concurrently, and/or the patient presentation process 700 may be incorporated into a more comprehensive procedure or process having additional functionality not described in detail herein. Moreover, one or more of the tasks shown and described in the context of FIG. 7 could be omitted from a practical embodiment of the patient presentation process 700 as long as the intended overall functionality remains intact.

In one or more exemplary embodiments, the patient presentation process 700 is performed in response to authenticating a user logging in to the patient monitoring application 110 executing on a computing device 102, 106. The illustrated patient presentation process 700 identifies or otherwise obtains the prioritization rules associated with the user (task 702). For example, in response to authenticating a user of a client electronic device 106 as a particular doctor or healthcare provider, the server 102 and/or the patient monitoring application 110 may query the database 104 using the authentication information or other identification information associated with that particular doctor or healthcare provider to obtain the prioritization rules associated with that doctor or provider from the monitoring settings data 124 maintained by the database 104.

The patient presentation process 700 also retrieves or otherwise obtains measurement data pertaining to patients associated with the user from the database (task 704). In this regard, the server 102 and/or the patient monitoring application 110 may query the database 104 using the authentication information or other identification information associated with a particular doctor or healthcare provider to identify patients associated therewith and retrieve measurement data for those patients from the patient data 120 maintained by the database 104. The measurement data may include, for each individual patient associated with the doctor or provider, measurement data samples for the physiological condition of the respective patient and/or one or more metrics indicative of the physiological condition of the respective patient that may be calculated based on the measurement data samples, such as, for example, an average measurement value, a median measurement value, percentile measurement values, a time in range percentage value, an amount of time above or below a threshold value, and/or the like.

Based on the patient measurement data, the patient presentation process 700 prioritizes or otherwise orders the patients associated with the user using the obtained prioritization rules (task 706). In this regard, the server 102 and/or the patient monitoring application 110 prioritizes, ranks, sorts, or otherwise orders patients in accordance with the respective priorities assigned to the respective adverse events that may be exhibited by those patients. For example, patients exhibiting one or more adverse events assigned a high priority may be classified or otherwise prioritized into a high priority patient subset, patients exhibiting one or more adverse events assigned a medium priority may be classified or otherwise prioritized into a medium priority patient subset, patients exhibiting one or more adverse events assigned a low priority may be classified or otherwise prioritized into a low priority patient subset, and patients that are not exhibiting any adverse events may be classified or otherwise prioritized into an asymptomatic patient subset. The high priority patient subset of patients may be prioritized above the medium priority patient subset, which is prioritized above the low priority patient subset, which, in turn, is prioritized above the asymptomatic patient subset. Within each subset, the server 102 and/or the patient monitoring application 110 may further prioritize patients within the respective subset based on the number, type, priority and/or severity of the adverse events exhibited by the respective patients and/or the measurement data associated with the respective patients within the subset. For example, within the high priority patient subset, any patients exhibiting two high priority adverse events may be ranked ahead of those exhibiting only one high priority adverse event, while any patient exhibiting one high priority adverse event and one lower priority adverse event may be ranked ahead of those not exhibiting any other adverse events. Patients may then be secondarily ranked or ordered based on their respective measurement data or metric values (e.g., in ascending order according to time in range percentage) or other factors.

Still referring to FIG. 7, in exemplary embodiments, after prioritizing the patients in accordance with the prioritization rules, the patient presentation process 700 continues by filtering the prioritized patient list based on a display threshold number of patients selected for presentation on the dashboard GUI display to thereby select or retain only a limited number of the highest priority patients for presentation on the dashboard GUI display (task 708). For example, referring to FIGS. 2-4, when the display number drop-down menu 203 sets the display threshold number equal to eight, any patients after the first eight patients in the prioritized list are removed or otherwise excluded, resulting in a filtered prioritized patient list that includes only the eight highest priority patients associated with the doctor or care provider. That said, it should be noted that the display threshold number may be customizable or otherwise configurable on a per-user basis, so that the number of patients presented within the patient list region 204 of the dashboard GUI display 200 may vary depending on the user.

Thereafter, the patient presentation process 700 continues by generating or otherwise providing a prioritized listing of patients associated with the user within the patient list region of the dashboard GUI display (task 710). In this regard, the server 102 and/or the patient monitoring application 110 populates the rows of the patient list region 204 with data or information associated with the respective patients of the filtered prioritized patient list according to their respective rankings. As described above, for each patient, the server 102 and/or the patient monitoring application 110 may query the database 104 for the patient's photograph, name, and/or other identifying information for populating patient identification columns 210, 212, 214 of the respective row associated with the patient. The server 102 and/or the patient monitoring application 110 may also query the database 104 for the electronic medical records associated with the patient for populating the patient notes column 230. The server 102 and/or the patient monitoring application 110 generates or otherwise provides a graphical representation of the physiological condition of the respective patient within the patient status column 216 that is rendered with a visually distinguishable characteristic corresponding to the relative priority or severity of the patient's associated symptoms, and the server 102 and/or the patient monitoring application 110 populates the prioritization reason column 218 with text or other indicia characterizing or summarizing the rationale (if any) for the patient's ranking within the patient list region 204.

As described above in the context of FIGS. 2-4, the loop defined by tasks 706, 708 and 710 may periodically or continually repeat during presentation of the patient monitoring dashboard GUI display to dynamically update the patient list region in real-time in response to changes in the measurement data associated with one or more patients. For example, in response to an updated sensor glucose measurement below 55 mg/dL for patient Bob Evans that indicates a hypoglycemic event below 55 mg/dL for a duration that exceeds 10 minutes, the server 102 and/or the patient monitoring application 110 dynamically updates the prioritized patient list to rank Bob Evans first among the doctor or care provider's associated patients since Bob Evans is currently exhibiting a higher priority adverse event than any of the doctor or care provider's other patients. The server 102 and/or the patient monitoring application 110 then updates the patient list region 204 in a corresponding manner to repopulate the first row in the patient list region 204 with values for the fields or columns corresponding to the newly highest priority patient Bob Evans, while repopulating the second row in the patient list region 204 with values for the fields or columns corresponding to the previous highest priority patient Kevin Adams, and so on until reaching the display threshold. Thus, the doctor or care provider may be readily apprised of the change in the status of the physiological condition of Bob Evans substantially in real-time.

It will be appreciated that by virtue of the patient presentation process 700 and the patient monitoring GUI displays described herein, a doctor or other healthcare provider may monitor the physiological condition of multiple patients substantially in real-time, with the patients being ordered or otherwise prioritized in a manner that facilitates the doctor or care provider quickly identifying those patients most in need of attention, thereby saving time while also alleviating the burdens associated with manually analyzing data for multiple patients. The doctor or care provider may then direct his or her to patients most in need of attention rather than devoting time or resources to patients that are asymptomatic or otherwise exhibiting normal physiology. In embodiments where a doctor or care provider has multiple patients with infusion devices utilizing closed-loop glucose control or otherwise using CGM devices, the doctor or care provider may utilize the patient monitoring dashboard GUI displays to more quickly identify which patients would most benefit from therapy modifications or other interventions, and then quickly navigate to view reports associated with those patients. For example, a doctor may identify patient Kevin Adams has having a relatively low time in range percentage than other patients, select the report button 228 to navigate directly to the report GUI display 500 for Kevin Adams from a patient monitoring GUI display 200, 400. The doctor may review the report GUI display 500 utilize GUI elements 512 provided on the report GUI display 500 to contact Kevin Adams to provide recommendations or therapy modifications to improve his time in range, and/or navigate back to the patient monitoring GUI display 200, 400 to utilize other GUI elements 222, 224, 226 to contact Kevin Adams. Thus, not only may the doctor's time may be more effectively devoted to patients most in need of attention, but the patient monitoring GUI display 200, 400 also facilitates expeditious analysis and/or intervention with those patients, thereby reducing the amount of time required for dealing with those patients, which, in turn, further increases the available time for attending to additional patients.

Figure 8:
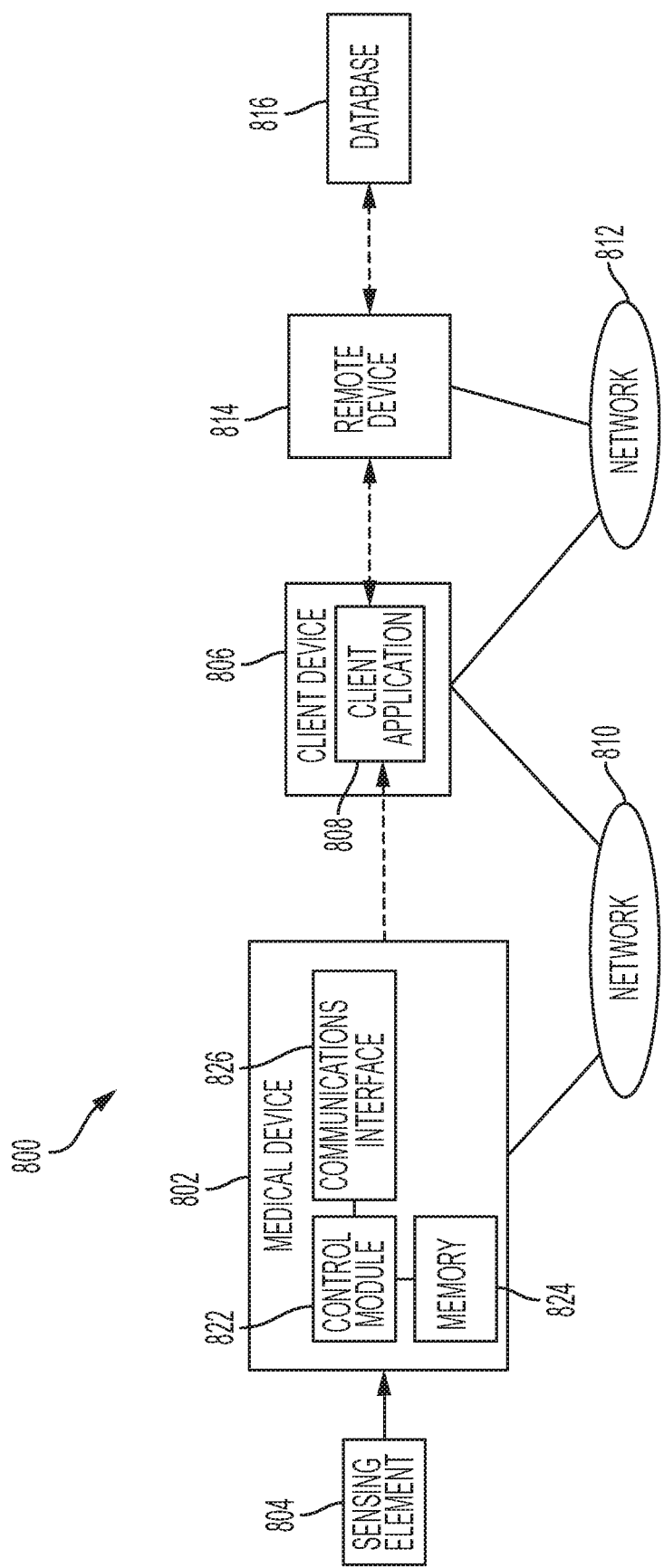
FIG. 8 is a block diagram of an exemplary patient monitoring system suitable for supporting or implementing the patient presentation process of FIG. 7 to generate a patient monitoring dashboard GUI display in accordance with one or more exemplary embodiments.

FIG. 8 depicts an exemplary embodiment of a patient monitoring system 800 suitable for use with implementing the patient presentation process 700 of FIG. 7 to provide a prioritized patient list within a patient monitoring dashboard GUI display, as described above. The patient monitoring system 800 includes a medical device 802 that is communicatively coupled to a sensing element 804 that is inserted into the body of a patient or otherwise worn by the patient to obtain measurement data indicative of a physiological condition in the body of the patient, such as a sensed glucose level. The medical device 802 is communicatively coupled to a client device 806 via a communications network 810, with the client device 806 being communicatively coupled to a remote device 814 via another communications network 812. In this regard, the client device 806 may function as an intermediary for uploading or otherwise providing measurement data from the medical device 802 to the remote device 814. It should be appreciated that FIG. 8 depicts a simplified representation of a patient monitoring system 800 for purposes of explanation and is not intended to limit the subject matter described herein in any way.

In exemplary embodiments, the client device 806 is realized as a mobile phone, a smartphone, a tablet computer, or other similar mobile electronic device; however, in other embodiments, the client device 806 may be realized as any sort of electronic device capable of communicating with the medical device 802 via network 810, such as a laptop or notebook computer, a desktop computer, or the like. In exemplary embodiments, the network 810 is realized as a Bluetooth network, a ZigBee network, or another suitable personal area network. That said, in other embodiments, the network 810 could be realized as a wireless ad hoc network, a wireless local area network (WLAN), or local area network (LAN). The client device 806 includes or is coupled to a display device, such as a monitor, screen, or another conventional electronic display, capable of graphically presenting data and/or information pertaining to the physiological condition of the patient. The client device 806 also includes or is otherwise associated with a user input device, such as a keyboard, a mouse, a touchscreen, or the like, capable of receiving input data and/or other information from the user of the client device 806.

In exemplary embodiments, a user, such as the patient, the patient's doctor or another healthcare provider, or the like, manipulates the client device 806 to execute a client application 808 that supports communicating with the medical device 802 via the network 810. In this regard, the client application 808 supports establishing a communications session with the medical device 802 on the network 810 and receiving data and/or information from the medical device 802 via the communications session. The medical device 802 may similarly execute or otherwise implement a corresponding application or process that supports establishing the communications session with the client application 808. The client application 808 generally represents a software module or another feature that is generated or otherwise implemented by the client device 806 to support the processes described herein. Accordingly, the client device 806 generally includes a processing system and a data storage element (or memory) capable of storing programming instructions for execution by the processing system, that, when read and executed, cause processing system to create, generate, or otherwise facilitate the client application 808 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 806 and the medical device 802 establish an association (or pairing) with one another over the network 810 to support subsequently establishing a point-to-point or peer-to-peer communications session between the medical device 802 and the client device 806 via the network 810. For example, in accordance with one embodiment, the network 810 is realized as a Bluetooth network, wherein the medical device 802 and the client device 806 are paired with one another (e.g., by obtaining and storing network identification information for one another) by performing a discovery procedure or another suitable pairing procedure. The pairing information obtained during the discovery procedure allows either of the medical device 802 or the client device 806 to initiate the establishment of a secure communications session via the network 810.

In one or more exemplary embodiments, the client application 808 is also configured to store or otherwise maintain an address and/or other identification information for the remote device 814 on the second network 812. In this regard, the second network 812 may be physically and/or logically distinct from the network 810, such as, for example, the Internet, a cellular network, a wide area network (WAN), or the like. The remote device 814 generally represents a server or other computing device configured to receive and analyze or otherwise monitor measurement data, event log data, and potentially other information obtained for the patient associated with the medical device 802. In exemplary embodiments, the remote device 814 is coupled to a database 816 configured to store or otherwise maintain data associated with individual patients. In practice, the remote device 814 may reside at a location that is physically distinct and/or separate from the medical device 802 and the client device 806, such as, for example, at a facility that is owned and/or operated by or otherwise affiliated with a manufacturer of the medical device 802. For purposes of explanation, but without limitation, the remote device 814 may alternatively be referred to herein as a server.

Still referring to FIG. 8, the sensing element 804 generally represents the component of the patient monitoring system 800 that is configured to generate, produce, or otherwise output one or more electrical signals indicative of a physiological condition that is sensed, measured, or otherwise quantified by the sensing element 804. In this regard, the physiological condition of a user influences a characteristic of the electrical signal output by the sensing element 804, such that the characteristic of the output signal corresponds to or is otherwise correlative to the physiological condition that the sensing element 804 is sensitive to. In exemplary embodiments, the sensing element 804 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 804.

The medical device 802 generally represents the component of the patient monitoring system 800 that is communicatively coupled to the output of the sensing element 804 to receive or otherwise obtain the measurement data samples from the sensing element 804 (e.g., the measured glucose and characteristic impedance values), store or otherwise maintain the measurement data samples, and upload or otherwise transmit the measurement data to the server 814 via the client device 806. In one or more embodiments, the medical device 802 is realized as an infusion device configured to deliver a fluid, such as insulin, to the body of the patient. That said, in other embodiments, the medical device 802 could be a standalone sensing or monitoring device separate and independent from an infusion device, such as, for example, a continuous glucose monitor (CGM), an interstitial glucose sensing arrangement, or similar device. It should be noted that although FIG. 8 depicts the medical device 802 and the sensing element 804 as separate components, in practice, the medical device 802 and the sensing element 804 may be integrated or otherwise combined to provide a unitary device that can be worn by the patient.

In exemplary embodiments, the medical device 802 includes a control module 822, a data storage element 824 (or memory), and a communications interface 826. The control module 822 generally represents the hardware, circuitry, logic, firmware and/or other component(s) of the medical device 802 that is coupled to the sensing element 804 to receive the electrical signals output by the sensing element 804 and perform or otherwise support various additional tasks, operations, functions and/or processes described herein. Depending on the embodiment, the control module 822 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 822 includes an analog-to-digital converter (ADC) or another similar sampling arrangement that samples or otherwise converts an output electrical signal received from the sensing element 804 into corresponding digital measurement data value. In other embodiments, the sensing element 804 may incorporate an ADC and output a digital measurement value.

The communications interface 826 generally represents the hardware, circuitry, logic, firmware and/or other components of the medical device 802 that are coupled to the control module 822 for outputting data and/or information from/to the medical device 802 to/from the client device 806. For example, the communications interface 826 may include or otherwise be coupled to one or more transceiver modules capable of supporting wireless communications between the medical device 802 and the client device 806. In exemplary embodiments, the communications interface 826 is realized as a Bluetooth transceiver or adapter configured to support Bluetooth Low Energy (BLE) communications.

In exemplary embodiments, the remote device 814 receives, from the client device 806, measurement data values associated with a particular patient (e.g., sensor glucose measurements, acceleration measurements, and the like) that were obtained using the sensing element 804, and the remote device 814 stores or otherwise maintains the historical measurement data in the database 816 in association with the patient (e.g., using one or more unique patient identifiers). Additionally, the remote device 814 may also receive, from or via the client device 806, meal data or other event log data that may be input or otherwise provided by the patient (e.g., via client application 808) and store or otherwise maintain historical meal data and other historical event or activity data associated with the patient in the database 816. In this regard, the meal data include, for example, a time or timestamp associated with a particular meal event, a meal type or other information indicative of the content or nutritional characteristics of the meal, and an indication of the size associated with the meal. When the medical device 802 is realized as an infusion device, the remote device 814 may also receive historical fluid delivery data corresponding to basal or bolus dosages of fluid delivered to the patient by the infusion device. For example, the client application 808 may communicate with an infusion device 802 to obtain insulin delivery dosage amounts and corresponding timestamps from the infusion device 802, and then upload the insulin delivery data to the remote device 814 for storage in association with the particular patient.

Referring to FIG. 8 with reference to FIGS. 1-4 and FIG. 7, multiple instances of devices 802, 804, 806 associated with different patients may continually upload measurement data, delivery data, event log data, and the like to the server 814 for storage in the database 816. Concurrently, a doctor or healthcare provider may utilize an instance of a client device 806 to login to the patient monitoring application 110 via the client application 808 to view a patient monitoring dashboard GUI display generated based on data associated with that doctor or healthcare provider's patients in the database 816. For example, the client application 808 may be realized as a web browser or similar local client application executed by the client device 806 that contacts the application server 102 using a networking protocol, such as the hypertext transport protocol (HTTP) or the like, to access or otherwise initiate an instance of the patient monitoring application 110 presented or otherwise provided within the client application 808 on the client device 806. The doctor or healthcare provider may utilize the patient monitoring dashboard GUI display to monitor his or her patients while the patient monitoring dashboard GUI display is dynamically updated or refreshed in real-time as the various devices 802, 804, 806 associated with the doctor or healthcare provider's patients concurrently upload new or updated data to the database 816.

Diabetes Data Management System Overview

Figure 9:
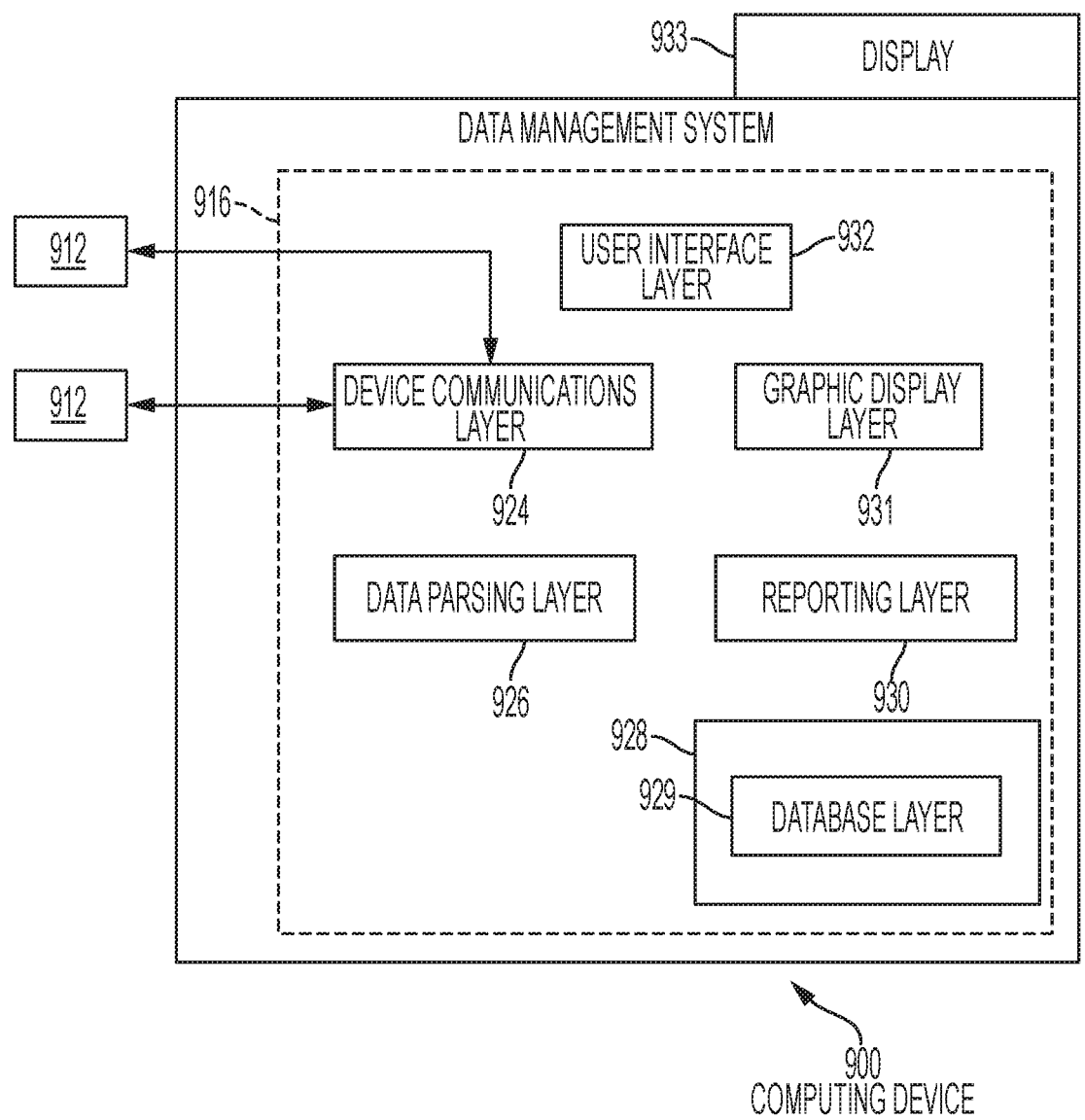
FIG. 9 depicts an embodiment of a computing device for a diabetes data management system in accordance with one or more embodiments.

FIG. 9 illustrates a computing device 900 including a display 933 suitable for presenting a patient monitoring dashboard GUI display 200, 400 as part of a diabetes data management system in conjunction with the patient presentation process 700 of FIG. 7 described above. The diabetes data management system (DDMS) may be referred to as the Medtronic MiniMed CARELINK™ system or as a medical data management system (MDMS) in some embodiments. The DDMS may be housed on a server or a plurality of servers which a user or a health care professional may access via a communications network via the Internet or the World Wide Web. Some models of the DDMS, which is described as an MDMS, are described in U.S. Patent Application Publication Nos. 2006/0031094 and 2013/0338630, which is herein incorporated by reference in their entirety.

While description of embodiments may be made in regard to monitoring medical or biological conditions for subjects having diabetes, the systems and processes herein are applicable to monitoring medical or biological conditions for cardiac subjects, cancer subjects, HIV subjects, subjects with other disease, infection, or controllable conditions, or various combinations thereof.

In embodiments of the invention, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 900. The computing device 900 may be coupled to a display 933. In some embodiments, the computing device 900 may be in a physical device separate from the display (such as in a personal computer, a mini-computer, etc.) In some embodiments, the computing device 900 may be in a single physical enclosure or device with the display 933 such as a laptop where the display 933 is integrated into the computing device. In embodiments of the invention, the computing device 900 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 900 may also be a server located on the Internet that is accessible via a browser installed on a laptop computer, desktop computer, a network computer, or a PDA. The computing device 900 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 9, the data management system 916 comprises a group of interrelated software modules or layers that specialize in different tasks. The system software includes a device communication layer 924, a data parsing layer 926, a database layer 928, database storage devices 929, a reporting layer 930, a graph display layer 931, and a user interface layer 932. The diabetes data management system may communicate with a plurality of subject support devices 912, two of which are illustrated in FIG. 9. Although the different reference numerals refer to a number of layers, (e.g., a device communication layer, a data parsing layer, a database layer), each layer may include a single software module or a plurality of software modules. For example, the device communications layer 924 may include a number of interacting software modules, libraries, etc. In embodiments of the invention, the data management system 916 may be installed onto a non-volatile storage area (memory such as flash memory, hard disk, removable hard, DVD-RW, CD-RW) of the computing device 900. If the data management system 916 is selected or initiated, the system 916 may be loaded into a volatile storage (memory such as DRAM, SRAM, RAM, DDRAM) for execution.

The device communication layer 924 is responsible for interfacing with at least one, and, in further embodiments, to a plurality of different types of subject support devices 912, such as, for example, blood glucose meters, glucose sensors/monitors, or an infusion pump. In one embodiment, the device communication layer 924 may be configured to communicate with a single type of subject support device 912. However, in more comprehensive embodiments, the device communication layer 924 is configured to communicate with multiple different types of subject support devices 912, such as devices made from multiple different manufacturers, multiple different models from a particular manufacturer and/or multiple different devices that provide different functions (such as infusion functions, sensing functions, metering functions, communication functions, user interface functions, or combinations thereof). By providing an ability to interface with multiple different types of subject support devices 912, the diabetes data management system 916 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 924 allows the DDMS 916 to receive information from and transmit information to or from each subject support device 912 in the system 916. Depending upon the embodiment and context of use, the type of information that may be communicated between the system 916 and device 912 may include, but is not limited to, data, programs, updated software, education materials, warning messages, notifications, device settings, therapy parameters, or the like. The device communication layer 924 may include suitable routines for detecting the type of subject support device 912 in communication with the system 916 and implementing appropriate communication protocols for that type of device 912. Alternatively, or in addition, the subject support device 912 may communicate information in packets or other data arrangements, where the communication includes a preamble or other portion that includes device identification information for identifying the type of the subject support device. Alternatively, or in addition, the subject support device 912 may include suitable user-operable interfaces for allowing a user to enter information, such as by selecting an optional icon or text or other device identifier that corresponds to the type of subject support device used by that user. Such information may be communicated to the system 916, through a network connection. In yet further embodiments, the system 916 may detect the type of subject support device 912 it is communicating with in the manner described above and then may send a message requiring the user to verify that the system 916 properly detected the type of subject support device being used by the user. For systems 916 that are capable of communicating with multiple different types of subject support devices 912, the device communication layer 924 may be capable of implementing multiple different communication protocols and selects a protocol that is appropriate for the detected type of subject support device.

The data-parsing layer 926 is responsible for validating the integrity of device data received and for inputting it correctly into a database 929. A cyclic redundancy check (CRC) process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 916 may compare received identification information with pre-stored information to evaluate whether the received information is from a valid source.

The database layer 928 may include a centralized database repository that is responsible for warehousing and archiving stored data in an organized format for later access, and retrieval. The database layer 928 operates with one or more data storage device(s) 929 suitable for storing and providing access to data in the manner described herein. Such data storage device(s) 929 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. Information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 916 or other entities, for analyzing group data or other forms of conglomerate data.

Embodiments of the database layer 928 and other components of the system 916 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 928 may be configured to limit access of each user to types of information pre-authorized for that user. For example, a subject may be allowed access to his or her individual medical information (with individual identifiers) stored by the database layer 928, but not allowed access to other subject's individual medical information (with individual identifiers). Similarly, a subject's authorized healthcare provider or payor entity may be provided access to some or all of the subject's individual medical information (with individual identifiers) stored by the database layer 928, but not allowed access to another individual's personal information. Also, an operator or administrator-user (on a separate computer communicating with the computing device 900) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 928 in the data storage devices 929.

In embodiments of the invention, the database layer 928 may store preference profiles. In the database layer 928, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 929 in the database layer. As described above, preference profiles may include various threshold values, monitoring period values, prioritization criteria, filtering criteria, and/or other user-specific values for parameters utilized by the patient presentation process 700 described above to generate a patient monitoring dashboard GUI display, such as patient monitoring dashboard GUI display 200, on the display 933 or a support device 912 in a personalized manner.

The DDMS 916 may measure, analyze, and track either blood glucose (BG) or sensor glucose (SG) readings for a user. In embodiments of the invention, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 930 may include a report wizard program that pulls data from selected locations in the database 929 and generates report information from the desired parameters of interest. The reporting layer 930 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar. In exemplary embodiments described herein, the reporting layer 930 also facilitates generation of a report, such as report GUI display 500 of FIG. 5.

In embodiments of the invention, the database layer 928 may calculate values for various medical information that is to be displayed on the reports generated by the report or reporting layer 930. For example, the database layer 928 may calculate average blood glucose or sensor glucose readings for specified timeframes. In embodiments of the invention, the reporting layer 930 may calculate values for medical or physical information that is to be displayed on the reports. For example, a user may select parameters which are then utilized by the reporting layer 930 to generate medical information values corresponding to the selected parameters. In other embodiments of the invention, the user may select a parameter profile that previously existed in the database layer 928.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs. In this manner, users may import data from the system 916 into further reporting tools familiar to the user. The reporting layer 930 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 930 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 916 may allow a user generating a report to designate the report as non-printable and/or non-transferable, whereby the system 916 will provide the report in a form that inhibits printing and/or electronic transfer.

The reporting layer 930 may transfer selected reports to the graph display layer 931. The graph display layer 931 receives information regarding the selected reports and converts the data into a format that can be displayed or shown on a display 933.

In embodiments of the invention, the reporting layer 930 may store a number of the user's parameters. Illustratively, the reporting layer 930 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 932 supports interactions with the end user, for example, for user login and data access, software navigation, data input, user selection of desired report types and the display of selected information. Users may also input parameters to be utilized in the selected reports via the user interface layer 932. Examples of users include but are not limited to: healthcare providers, healthcare payer entities, system operators or administrators, researchers, business entities, healthcare institutions and organizations, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 932 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 916, depending upon the embodiment of use.

In another example embodiment, where the DDMS 916 is located on one computing device 900, the user interface layer 932 provides a number of menus to the user to navigate through the DDMS. These menus may be created utilizing any menu format, including but not limited to HTML, XML, or Active Server pages. A user may access the DDMS 916 to perform one or more of a variety of tasks, such as accessing general information made available on a website to all subjects or groups of subjects. The user interface layer 932 of the DDMS 916 may allow a user to access specific information or to generate reports regarding that subject's medical condition or that subject's medical device(s) 912, to transfer data or other information from that subject's support device(s) 912 to the system 916, to transfer data, programs, program updates or other information from the system 916 to the subject's support device(s) 912, to manually enter information into the system 916, to engage in a remote consultation exchange with a healthcare provider, or to modify the custom settings in a subject's supported device and/or in a subject's DDMS/MDMS data file.

The system 916 may provide access to different optional resources or activities (including accessing different information items and services) to different users and to different types or groups of users, such that each user may have a customized experience and/or each type or group of users (e.g., all users, diabetic users, cardio users, healthcare provider-user or payor-user, or the like) may have a different set of information items or services available on the system. The system 916 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 916, based on the type of user and/or the identity of the user.

Upon entering successful verification of the user's identification information and password, the user may be provided access to secure, personalized information stored on the DDMS 916. For example, the user may be provided access to a secure, personalized location in the DDMS 916 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 912 to the system 916, manually enter additional data into the system 916, modify the subject's custom settings, and/or view and print reports. Reports may include data specific to the subject's condition, including but not limited to, data obtained from the subject's support device(s) 912, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 929) employed by the database layer 928.

The user may select an option to transfer (send) device data to the medical data management system 916. If the system 916 receives a user's request to transfer device data to the system, the system 916 may provide the user with step-by-step instructions on how to transfer data from the subject's supported device(s) 912. For example, the DDMS 916 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 912 used by the subject. The system 916 employs that information to select the stored instruction set(s) associated with the particular subject's support device(s) 912 for display to the user.

Other activities or resources available to the user on the system 916 may include an option for manually entering information to the DDMS/MDMS 916. For example, from the user's personalized menu or location, the user may select an option to manually enter additional information into the system 916.

Further optional activities or resources may be available to the user on the DDMS 916. For example, from the user's personalized menu, the user may select an option to receive data, software, software updates, treatment recommendations or other information from the system 916 on the subject's support device(s) 912. If the system 916 receives a request from a user to receive data, software, software updates, treatment recommendations or other information, the system 916 may provide the user with a list or other arrangement of multiple selectable icons or other indicia representing available data, software, software updates or other information available to the user.

Yet further optional activities or resources may be available to the user on the medical data management system 916 including, for example, an option for the user to customize or otherwise further personalize the user's personalized location or menu. In particular, from the user's personalized location, the user may select an option to customize parameters for the user. In addition, the user may create profiles of customizable parameters. When the system 916 receives such a request from a user, the system 916 may provide the user with a list or other arrangement of multiple selectable icons or other indicia representing parameters that may be modified to accommodate the user's preferences. When a user selects one or more of the icons or other indicia, the system 916 may receive the user's request and makes the requested modification.

Infusion System Overview

Figure 10:
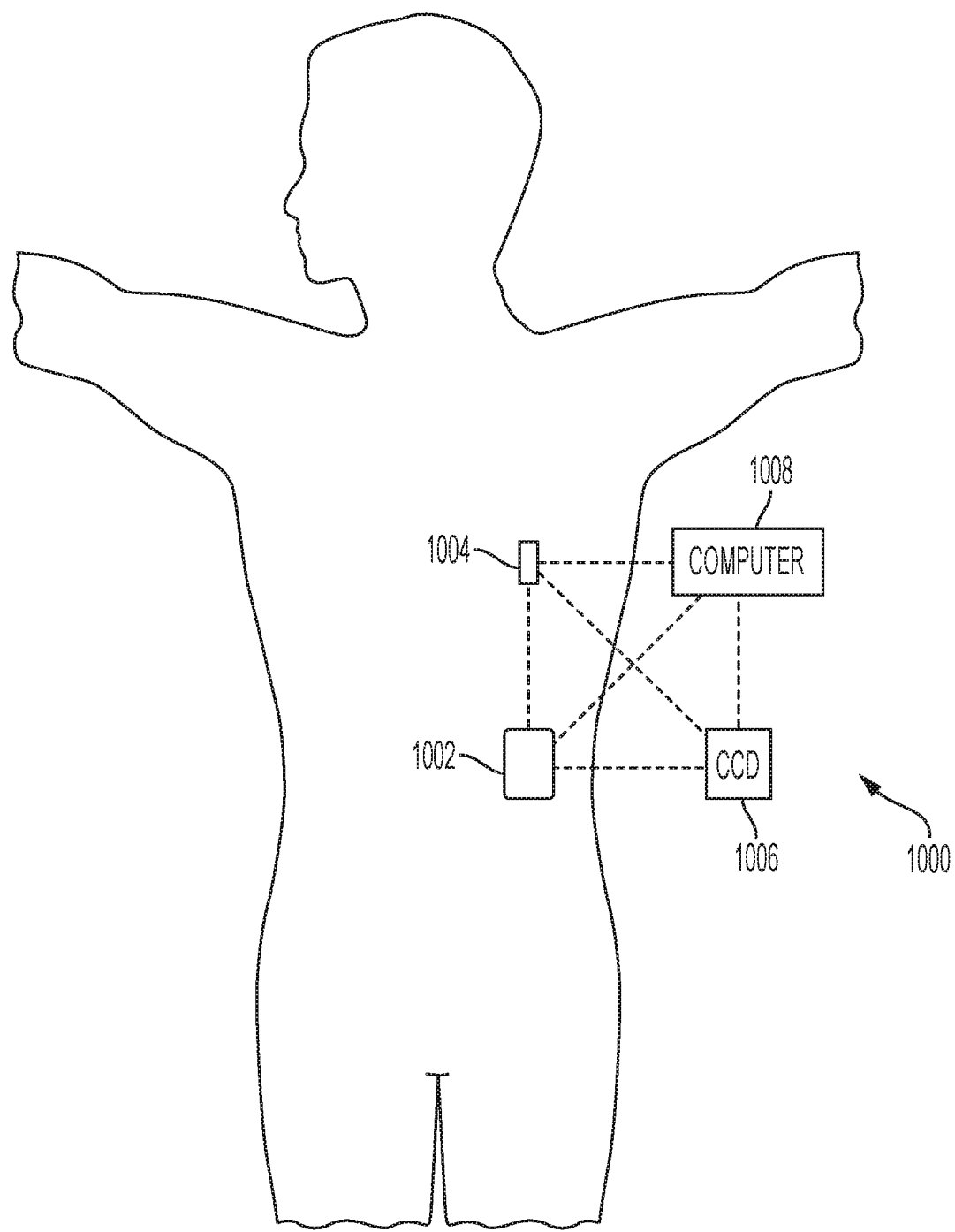
FIG. 10 depicts an exemplary embodiment of an infusion system.

FIG. 10 depicts one exemplary embodiment of an infusion system 1000 that includes, without limitation, a fluid infusion device (or infusion pump) 1002, a sensing arrangement 1004, a command control device (CCD) 1006, and a computer 1008, which could be realized as any one of the computing devices 102, 106, 806, 812, 900, 912 described above. The components of an infusion system 1000 may be realized using different platforms, designs, and configurations, and the embodiment shown in FIG. 10 is not exhaustive or limiting. In practice, the infusion device 1002 and the sensing arrangement 1004 are secured at desired locations on the body of a user (or patient), as illustrated in FIG. 10. In this regard, the locations at which the infusion device 1002 and the sensing arrangement 1004 are secured to the body of the user in FIG. 10 are provided only as a representative, non-limiting, example.

In the illustrated embodiment of FIG. 10, the infusion device 1002 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 1004 generally represents the components of the infusion system 1000 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 1004 may include electronics and enzymes reactive to a biological or physiological condition of the user, such as a blood glucose level, or the like, and provide data indicative of the blood glucose level to the infusion device 1002, the CCD 1006 and/or the computer 1008. For example, the infusion device 1002, the CCD 1006 and/or the computer 1008 may include a display for presenting information or data to the user based on the sensor data received from the sensing arrangement 1004, such as, for example, a current glucose level of the user, a graph or chart of the user's glucose level versus time, device status indicators, alert messages, or the like. In other embodiments, the infusion device 1002, the CCD 1006 and/or the computer 1008 may include electronics and software that are configured to analyze sensor data and operate the infusion device 1002 to deliver fluid to the body of the user based on the sensor data and/or preprogrammed delivery routines. Thus, in exemplary embodiments, one or more of the infusion device 1002, the sensing arrangement 1004, the CCD 1006, and/or the computer 1008 includes a transmitter, a receiver, and/or other transceiver electronics that allow for communication with other components of the infusion system 1000, so that the sensing arrangement 1004 may transmit sensor data or monitor data to one or more of the infusion device 1002, the CCD 1006 and/or the computer 1008.

Still referring to FIG. 10, in various embodiments, the sensing arrangement 1004 may be secured to the body of the user or embedded in the body of the user at a location that is remote from the location at which the infusion device 1002 is secured to the body of the user. In various other embodiments, the sensing arrangement 1004 may be incorporated within the infusion device 1002. In other embodiments, the sensing arrangement 1004 may be separate and apart from the infusion device 1002, and may be, for example, part of the CCD 1006. In such embodiments, the sensing arrangement 1004 may be configured to receive a biological sample, analyte, or the like, to measure a condition of the user.

In various embodiments, the CCD 1006 and/or the computer 1008 may include electronics and other components configured to perform processing, delivery routine storage, and to control the infusion device 1002 in a manner that is influenced by sensor data measured by and/or received from the sensing arrangement 1004. By including control functions in the CCD 1006 and/or the computer 1008, the infusion device 1002 may be made with more simplified electronics. However, in other embodiments, the infusion device 1002 may include all control functions, and may operate without the CCD 1006 and/or the computer 1008. In various embodiments, the CCD 1006 may be a portable electronic device. In addition, in various embodiments, the infusion device 1002 and/or the sensing arrangement 1004 may be configured to transmit data to the CCD 1006 and/or the computer 1008 for display or processing of the data by the CCD 1006 and/or the computer 1008.

In some embodiments, the CCD 1006 and/or the computer 1008 may provide information to the user that facilitates the user's subsequent use of the infusion device 1002. For example, the CCD 1006 may provide information to the user to allow the user to determine the rate or dose of medication to be administered into the user's body. In other embodiments, the CCD 1006 may provide information to the infusion device 1002 to autonomously control the rate or dose of medication administered into the body of the user. In some embodiments, the sensing arrangement 1004 may be integrated into the CCD 1006. Such embodiments may allow the user to monitor a condition by providing, for example, a sample of his or her blood to the sensing arrangement 1004 to assess his or her condition. In some embodiments, the sensing arrangement 1004 and the CCD 1006 may be used for determining glucose levels in the blood and/or body fluids of the user without the use of, or necessity of, a wire or cable connection between the infusion device 1002 and the sensing arrangement 1004 and/or the CCD 1006.

In one or more exemplary embodiments, the sensing arrangement 1004 and/or the infusion device 1002 are cooperatively configured to utilize a closed-loop system for delivering fluid to the user. In such embodiments, the sensing arrangement 1004 is configured to sense or measure a condition of the user, such as, blood glucose level or the like. The infusion device 1002 is configured to deliver fluid in response to the condition sensed by the sensing arrangement 1004. In turn, the sensing arrangement 1004 continues to sense or otherwise quantify a current condition of the user, thereby allowing the infusion device 1002 to deliver fluid continuously in response to the condition currently (or most recently) sensed by the sensing arrangement 1004 indefinitely. In some embodiments, the sensing arrangement 1004 and/or the infusion device 1002 may be configured to utilize the closed-loop system only for a portion of the day, for example only when the user is asleep or awake.

Figure 11:
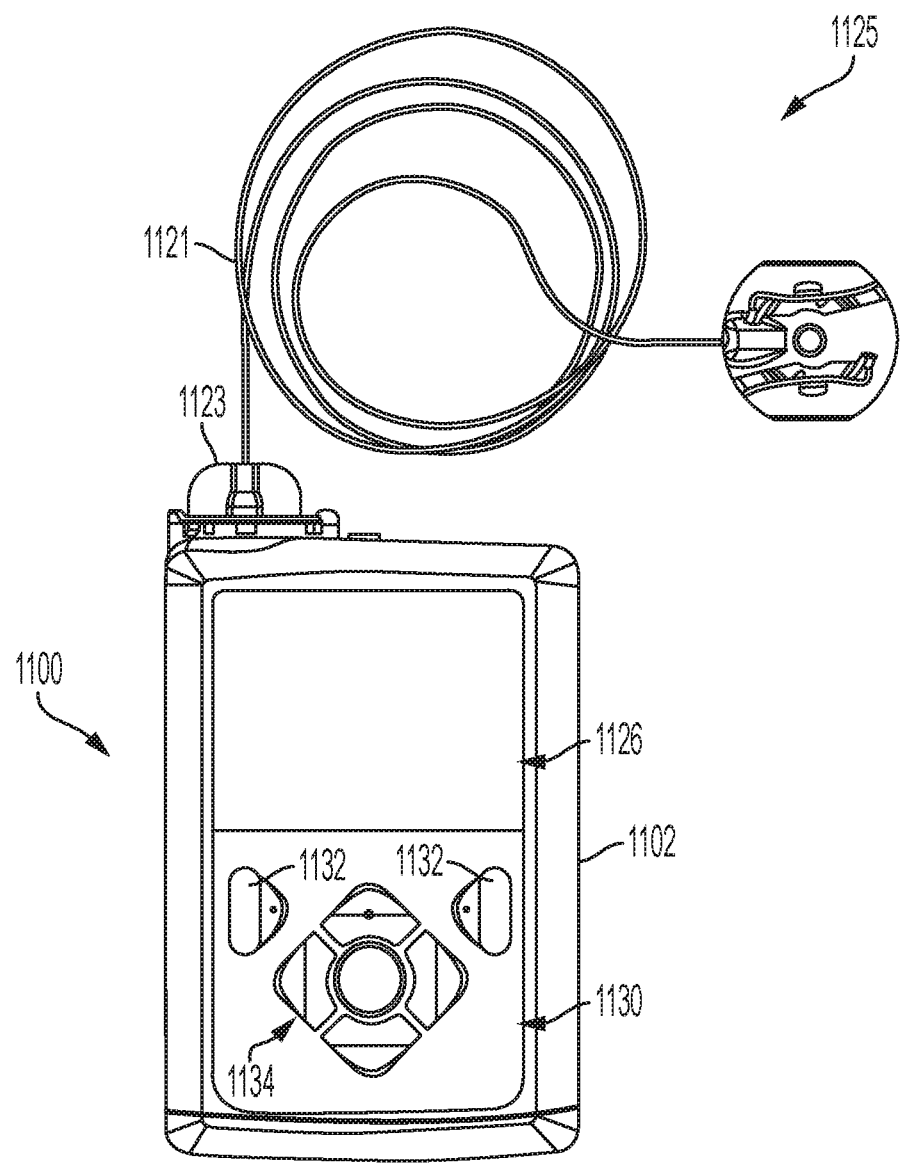
FIG. 11 depicts a plan view of an exemplary embodiment of a fluid infusion device suitable for use in the infusion system of FIG. 10.
Figure 12:
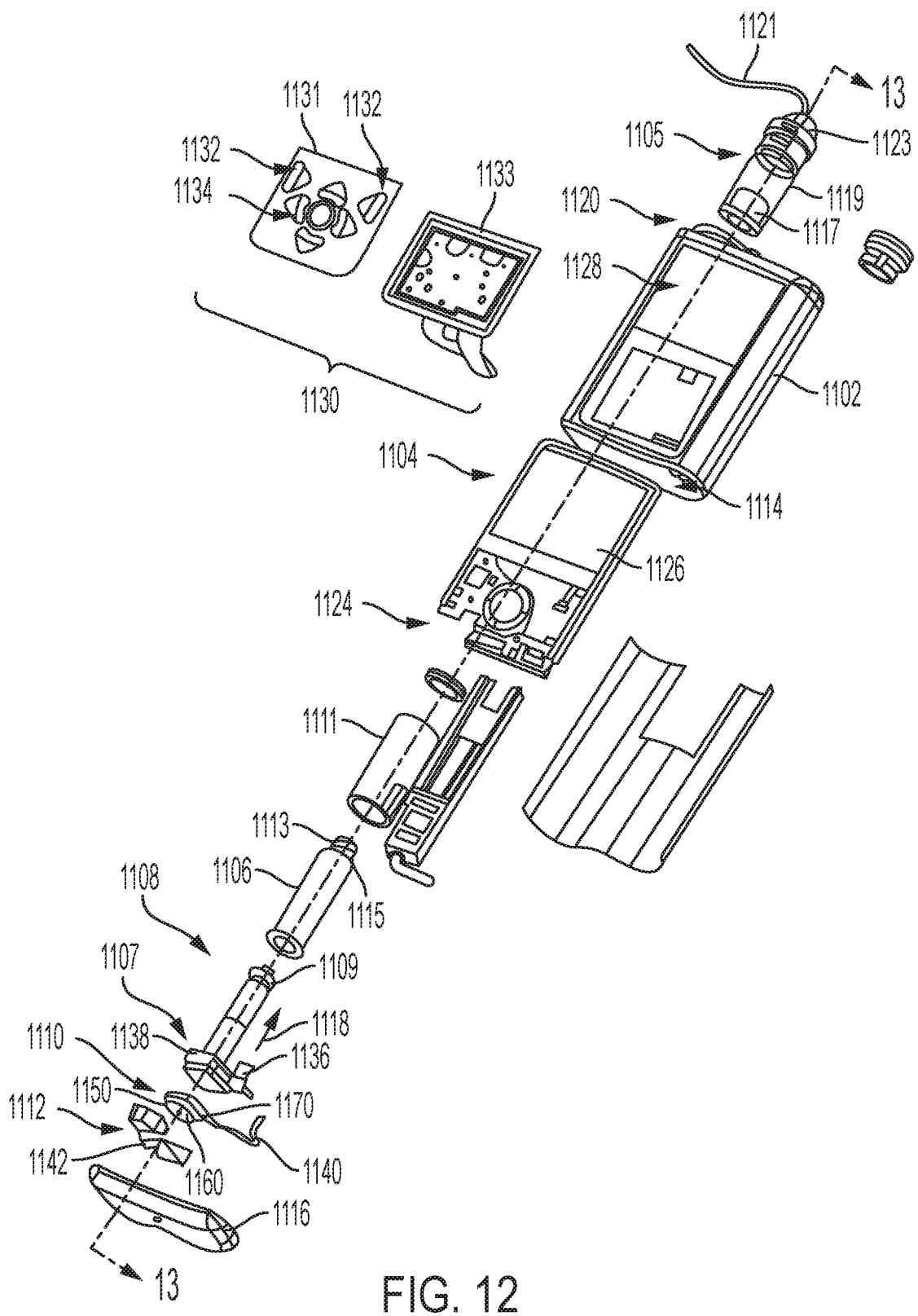
FIG. 12 is an exploded perspective view of the fluid infusion device of FIG. 11.
Figure 13:
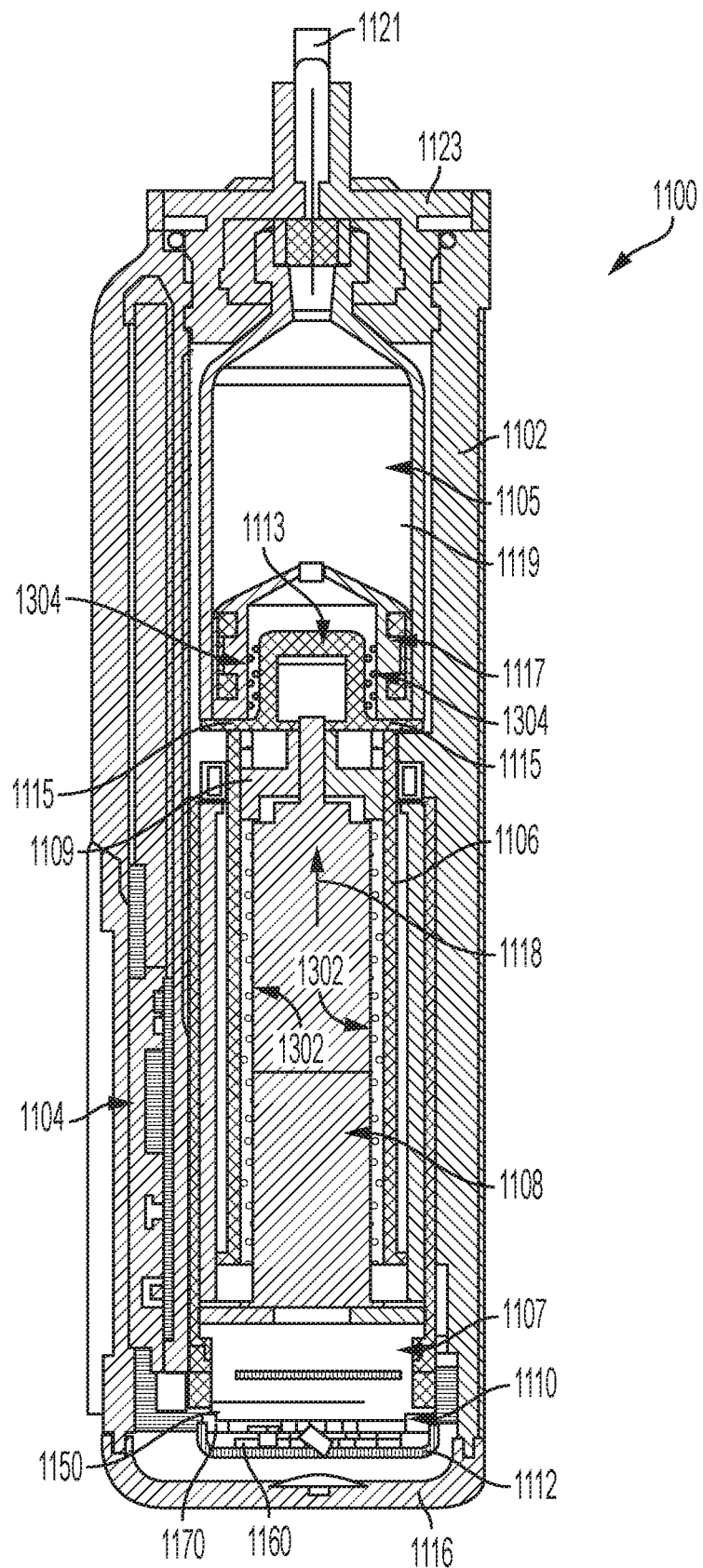
FIG. 13 is a cross-sectional view of the fluid infusion device of FIGS. 11-12 as viewed along line 13-13 in FIG. 12 when assembled with a reservoir inserted in the infusion device.

FIGS. 11-13 depict one exemplary embodiment of a fluid infusion device 1100 (or alternatively, infusion pump) suitable for use in an infusion system, such as, for example, as infusion device 1002 in the infusion system 1000 of FIG. 10. The fluid infusion device 1100 is a portable medical device designed to be carried or worn by a patient (or user), and the fluid infusion device 1100 may leverage any number of conventional features, components, elements, and characteristics of existing fluid infusion devices. It should be appreciated that FIGS. 11-13 depict some aspects of the infusion device 1100 in a simplified manner; in practice, the infusion device 1100 could include additional elements, features, or components that are not shown or described in detail herein.

As best illustrated in FIGS. 11-12, the illustrated embodiment of the fluid infusion device 1100 includes a housing 1102 adapted to receive a fluid-containing reservoir 1105. An opening 1120 in the housing 1102 accommodates a fitting 1123 (or cap) for the reservoir 1105, with the fitting 1123 being configured to mate or otherwise interface with tubing 1121 of an infusion set 1125 that provides a fluid path to/from the body of the user. In this manner, fluid communication from the interior of the reservoir 1105 to the user is established via the tubing 1121. The illustrated fluid infusion device 1100 includes a human-machine interface (HMI) 1130 (or user interface) that includes elements 1132, 1134 that can be manipulated by the user to administer a bolus of fluid (e.g., insulin), to change therapy settings, to change user preferences, to select display features, and the like. The infusion device also includes a display element 1126, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 1102 is formed from a substantially rigid material having a hollow interior 1114 adapted to allow an electronics assembly 1104, a sliding member (or slide) 1106, a drive system 1108, a sensor assembly 1110, and a drive system capping member 1112 to be disposed therein in addition to the reservoir 1105, with the contents of the housing 1102 being enclosed by a housing capping member 1116. The opening 1120, the slide 1106, and the drive system 1108 are coaxially aligned in an axial direction (indicated by arrow 1118), whereby the drive system 1108 facilitates linear displacement of the slide 1106 in the axial direction 1118 to dispense fluid from the reservoir 1105 (after the reservoir 1105 has been inserted into opening 1120), with the sensor assembly 1110 being configured to measure axial forces (e.g., forces aligned with the axial direction 1118) exerted on the sensor assembly 1110 responsive to operating the drive system 1108 to displace the slide 1106. In various embodiments, the sensor assembly 1110 may be utilized to detect one or more of the following: an occlusion in a fluid path that slows, prevents, or otherwise degrades fluid delivery from the reservoir 1105 to a user's body; when the reservoir 1105 is empty; when the slide 1106 is properly seated with the reservoir 1105; when a fluid dose has been delivered; when the infusion pump 1100 is subjected to shock or vibration; when the infusion pump 1100 requires maintenance.

Depending on the embodiment, the fluid-containing reservoir 1105 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 12-13, the reservoir 1105 typically includes a reservoir barrel 1119 that contains the fluid and is concentrically and/or coaxially aligned with the slide 1106 (e.g., in the axial direction 1118) when the reservoir 1105 is inserted into the infusion pump 1100. The end of the reservoir 1105 proximate the opening 1120 may include or otherwise mate with the fitting 1123, which secures the reservoir 1105 in the housing 1102 and prevents displacement of the reservoir 1105 in the axial direction 1118 with respect to the housing 1102 after the reservoir 1105 is inserted into the housing 1102. As described above, the fitting 1123 extends from (or through) the opening 1120 of the housing 1102 and mates with tubing 1121 to establish fluid communication from the interior of the reservoir 1105 (e.g., reservoir barrel 1119) to the user via the tubing 1121 and infusion set 1125. The opposing end of the reservoir 1105 proximate the slide 1106 includes a plunger 1117 (or stopper) positioned to push fluid from inside the barrel 1119 of the reservoir 1105 along a fluid path through tubing 1121 to a user. The slide 1106 is configured to mechanically couple or otherwise engage with the plunger 1117, thereby becoming seated with the plunger 1117 and/or reservoir 1105. Fluid is forced from the reservoir 1105 via tubing 1121 as the drive system 1108 is operated to displace the slide 1106 in the axial direction 1118 toward the opening 1120 in the housing 1102.

In the illustrated embodiment of FIGS. 12-13, the drive system 1108 includes a motor assembly 1107 and a drive screw 1109. The motor assembly 1107 includes a motor that is coupled to drive train components of the drive system 1108 that are configured to convert rotational motor motion to a translational displacement of the slide 1106 in the axial direction 1118, and thereby engaging and displacing the plunger 1117 of the reservoir 1105 in the axial direction 1118. In some embodiments, the motor assembly 1107 may also be powered to translate the slide 1106 in the opposing direction (e.g., the direction opposite direction 1118) to retract and/or detach from the reservoir 1105 to allow the reservoir 1105 to be replaced. In exemplary embodiments, the motor assembly 1107 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 1105.

As best shown in FIG. 13, the drive screw 1109 mates with threads 1302 internal to the slide 1106. When the motor assembly 1107 is powered and operated, the drive screw 1109 rotates, and the slide 1106 is forced to translate in the axial direction 1118. In an exemplary embodiment, the infusion pump 1100 includes a sleeve 1111 to prevent the slide 1106 from rotating when the drive screw 1109 of the drive system 1108 rotates. Thus, rotation of the drive screw 1109 causes the slide 1106 to extend or retract relative to the drive motor assembly 1107. When the fluid infusion device is assembled and operational, the slide 1106 contacts the plunger 1117 to engage the reservoir 1105 and control delivery of fluid from the infusion pump 1100. In an exemplary embodiment, the shoulder portion 1115 of the slide 1106 contacts or otherwise engages the plunger 1117 to displace the plunger 1117 in the axial direction 1118. In alternative embodiments, the slide 1106 may include a threaded tip 1113 capable of being detachably engaged with internal threads 1304 on the plunger 1117 of the reservoir 1105.

As illustrated in FIG. 12, the electronics assembly 1104 includes control electronics 1124 coupled to the display element 1126, with the housing 1102 including a transparent window portion 1128 that is aligned with the display element 1126 to allow the display 1126 to be viewed by the user when the electronics assembly 1104 is disposed within the interior 1114 of the housing 1102. The control electronics 1124 generally represent the hardware, firmware, processing logic and/or software (or combinations thereof) configured to control operation of the motor assembly 1107 and/or drive system 1108, as described in greater detail below in the context of FIG. 14. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 1124 includes one or more programmable controllers that may be programmed to control operation of the infusion pump 1100.

The motor assembly 1107 includes one or more electrical leads 1136 adapted to be electrically coupled to the electronics assembly 1104 to establish communication between the control electronics 1124 and the motor assembly 1107. In response to command signals from the control electronics 1124 that operate a motor driver (e.g., a power converter) to regulate the amount of power supplied to the motor from a power supply, the motor actuates the drive train components of the drive system 1108 to displace the slide 1106 in the axial direction 1118 to force fluid from the reservoir 1105 along a fluid path (including tubing 1121 and an infusion set), thereby administering doses of the fluid contained in the reservoir 1105 into the user's body. Preferably, the power supply is realized one or more batteries contained within the housing 1102. Alternatively, the power supply may be a solar panel, capacitor, AC or DC power supplied through a power cord, or the like. In some embodiments, the control electronics 1124 may operate the motor of the motor assembly 1107 and/or drive system 1108 in a stepwise manner, typically on an intermittent basis; to administer discrete precise doses of the fluid to the user according to programmed delivery profiles.

Referring to FIGS. 11-13, as described above, the user interface 1130 includes HMI elements, such as buttons 1132 and a directional pad 1134, that are formed on a graphic keypad overlay 1131 that overlies a keypad assembly 1133, which includes features corresponding to the buttons 1132, directional pad 1134 or other user interface items indicated by the graphic keypad overlay 1131. When assembled, the keypad assembly 1133 is coupled to the control electronics 1124, thereby allowing the HMI elements 1132, 1134 to be manipulated by the user to interact with the control electronics 1124 and control operation of the infusion pump 1100, for example, to administer a bolus of insulin, to change therapy settings, to change user preferences, to select display features, to set or disable alarms and reminders, and the like. In this regard, the control electronics 1124 maintains and/or provides information to the display 1126 regarding program parameters, delivery profiles, pump operation, alarms, warnings, statuses, or the like, which may be adjusted using the HMI elements 1132, 1134. In various embodiments, the HMI elements 1132, 1134 may be realized as physical objects (e.g., buttons, knobs, joysticks, and the like) or virtual objects (e.g., using touch-sensing and/or proximity-sensing technologies). For example, in some embodiments, the display 1126 may be realized as a touch screen or touch-sensitive display, and in such embodiments, the features and/or functionality of the HMI elements 1132, 1134 may be integrated into the display 1126 and the HMI 1130 may not be present. In some embodiments, the electronics assembly 1104 may also include alert generating elements coupled to the control electronics 1124 and suitably configured to generate one or more types of feedback, such as, without limitation: audible feedback; visual feedback; haptic (physical) feedback; or the like.

Referring to FIGS. 12-13, in accordance with one or more embodiments, the sensor assembly 1110 includes a back plate structure 1150 and a loading element 1160. The loading element 1160 is disposed between the capping member 1112 and a beam structure 1170 that includes one or more beams having sensing elements disposed thereon that are influenced by compressive force applied to the sensor assembly 1110 that deflects the one or more beams. In exemplary embodiments, the back plate structure 1150 is affixed, adhered, mounted, or otherwise mechanically coupled to the bottom surface 1138 of the drive system 1108 such that the back plate structure 1150 resides between the bottom surface 1138 of the drive system 1108 and the housing cap 1116. The drive system capping member 1112 is contoured to accommodate and conform to the bottom of the sensor assembly 1110 and the drive system 1108. The drive system capping member 1112 may be affixed to the interior of the housing 1102 to prevent displacement of the sensor assembly 1110 in the direction opposite the direction of force provided by the drive system 1108 (e.g., the direction opposite direction 1118). Thus, the sensor assembly 1110 is positioned between the motor assembly 1107 and secured by the capping member 1112, which prevents displacement of the sensor assembly 1110 in a downward direction opposite the direction of arrow 1118, such that the sensor assembly 1110 is subjected to a reactionary compressive force when the drive system 1108 and/or motor assembly 1107 is operated to displace the slide 1106 in the axial direction 1118 in opposition to the fluid pressure in the reservoir 1105. Under normal operating conditions, the compressive force applied to the sensor assembly 1110 is correlated with the fluid pressure in the reservoir 1105. As shown, electrical leads 1140 are adapted to electrically couple the sensing elements of the sensor assembly 1110 to the electronics assembly 1104 to establish communication to the control electronics 1124, wherein the control electronics 1124 are configured to measure, receive, or otherwise obtain electrical signals from the sensing elements of the sensor assembly 1110 that are indicative of the force applied by the drive system 1108 in the axial direction 1118.

Figure 14:
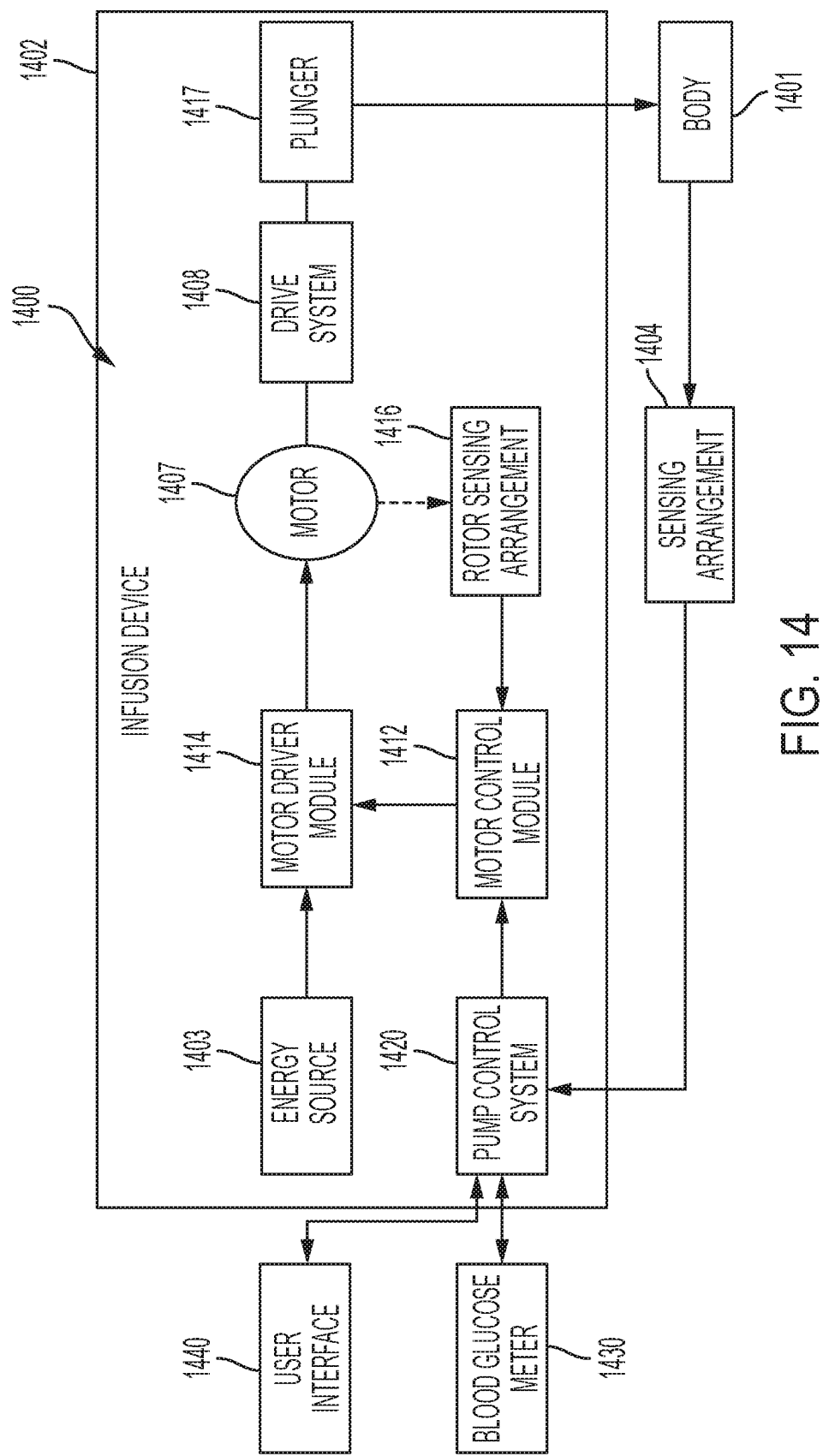
FIG. 14 is a block diagram of an exemplary control system suitable for use in a fluid infusion device, such as the fluid infusion device of FIG. 10 or 11.

FIG. 14 depicts an exemplary embodiment of a control system 1400 suitable for use with an infusion device 1402, such as any one of the infusion devices 802, 1002, 1100 described above. The control system 1400 is capable of controlling or otherwise regulating a physiological condition in the body 1401 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 1404 (e.g., sensing arrangement 1004) communicatively coupled to the infusion device 1402. However, it should be noted that in alternative embodiments, the condition being regulated by the control system 1400 may be correlative to the measured values obtained by the sensing arrangement 1404. That said, for clarity and purposes of explanation, the subject matter may be described herein in the context of the sensing arrangement 1404 being realized as a glucose sensing arrangement that senses, detects, measures or otherwise quantifies the user's glucose level, which is being regulated in the body 1401 of the user by the control system 1400.

In exemplary embodiments, the sensing arrangement 1404 includes one or more interstitial glucose sensing elements that generate or otherwise output electrical signals having a signal characteristic that is correlative to, influenced by, or otherwise indicative of the relative interstitial fluid glucose level in the body 1401 of the user. The output electrical signals are filtered or otherwise processed to obtain a measurement value indicative of the user's interstitial fluid glucose level. In exemplary embodiments, a blood glucose meter 1430, such as a finger stick device, is utilized to directly sense, detect, measure or otherwise quantify the blood glucose in the body 1401 of the user. In this regard, the blood glucose meter 1430 outputs or otherwise provides a measured blood glucose value that may be utilized as a reference measurement for calibrating the sensing arrangement 1404 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 1404 may alternatively be referred to herein as the sensor glucose value, the sensed glucose value, or variants thereof.

In the illustrated embodiment, the pump control system 1420 generally represents the electronics and other components of the infusion device 1402 that control operation of the fluid infusion device 1402 according to a desired infusion delivery program in a manner that is influenced by the sensed glucose value indicative of a current glucose level in the body 1401 of the user. For example, to support a closed-loop operating mode, the pump control system 1420 maintains, receives, or otherwise obtains a target or commanded glucose value, and automatically generates or otherwise determines dosage commands for operating an actuation arrangement, such as a motor 1407, to displace the plunger 1417 and deliver insulin to the body 1401 of the user based on the difference between a sensed glucose value and the target glucose value. In other operating modes, the pump control system 1420 may generate or otherwise determine dosage commands configured to maintain the sensed glucose value below an upper glucose limit, above a lower glucose limit, or otherwise within a desired range of glucose values. In practice, the infusion device 1402 may store or otherwise maintain the target value, upper and/or lower glucose limit(s), and/or other glucose threshold value(s) in a data storage element accessible to the pump control system 1420.

The target glucose value and other threshold glucose values may be received from an external component (e.g., CCD 1006 and/or computing device 1008) or be input by a user via a user interface element 1440 associated with the infusion device 1402. In practice, the one or more user interface element(s) 1440 associated with the infusion device 1402 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 1440 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 14 depicts the user interface element(s) 1440 as being separate from the infusion device 1402, in practice, one or more of the user interface element(s) 1440 may be integrated with the infusion device 1402. Furthermore, in some embodiments, one or more user interface element(s) 1440 are integrated with the sensing arrangement 1404 in addition to and/or in alternative to the user interface element(s) 1440 integrated with the infusion device 1402. The user interface element(s) 1440 may be manipulated by the user to operate the infusion device 1402 to deliver correction boluses, adjust target and/or threshold values, modify the delivery control scheme or operating mode, and the like, as desired.

Still referring to FIG. 14, in the illustrated embodiment, the infusion device 1402 includes a motor control module 1412 coupled to a motor 1407 (e.g., motor assembly 1107) that is operable to displace a plunger 1417 (e.g., plunger 1117) in a reservoir (e.g., reservoir 1105) and provide a desired amount of fluid to the body 1401 of a user. In this regard, displacement of the plunger 1417 results in the delivery of a fluid that is capable of influencing the condition in the body 1401 of the user to the body 1401 of the user via a fluid delivery path (e.g., via tubing 1121 of an infusion set 1125). A motor driver module 1414 is coupled between an energy source 1403 and the motor 1407. The motor control module 1412 is coupled to the motor driver module 1414, and the motor control module 1412 generates or otherwise provides command signals that operate the motor driver module 1414 to provide current (or power) from the energy source 1403 to the motor 1407 to displace the plunger 1417 in response to receiving, from a pump control system 1420, a dosage command indicative of the desired amount of fluid to be delivered.

In exemplary embodiments, the energy source 1403 is realized as a battery housed within the infusion device 1402 (e.g., within housing 1102) that provides direct current (DC) power. In this regard, the motor driver module 1414 generally represents the combination of circuitry, hardware and/or other electrical components configured to convert or otherwise transfer DC power provided by the energy source 1403 into alternating electrical signals applied to respective phases of the stator windings of the motor 1407 that result in current flowing through the stator windings that generates a stator magnetic field and causes the rotor of the motor 1407 to rotate. The motor control module 1412 is configured to receive or otherwise obtain a commanded dosage from the pump control system 1420, convert the commanded dosage to a commanded translational displacement of the plunger 1417, and command, signal, or otherwise operate the motor driver module 1414 to cause the rotor of the motor 1407 to rotate by an amount that produces the commanded translational displacement of the plunger 1417. For example, the motor control module 1412 may determine an amount of rotation of the rotor required to produce translational displacement of the plunger 1417 that achieves the commanded dosage received from the pump control system 1420. Based on the current rotational position (or orientation) of the rotor with respect to the stator that is indicated by the output of the rotor sensing arrangement 1416, the motor control module 1412 determines the appropriate sequence of alternating electrical signals to be applied to the respective phases of the stator windings that should rotate the rotor by the determined amount of rotation from its current position (or orientation). In embodiments where the motor 1407 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 1412 operates the motor driver module 1414 to apply the determined alternating electrical signals (e.g., the command signals) to the stator windings of the motor 1407 to achieve the desired delivery of fluid to the user.

When the motor control module 1412 is operating the motor driver module 1414, current flows from the energy source 1403 through the stator windings of the motor 1407 to produce a stator magnetic field that interacts with the rotor magnetic field. In some embodiments, after the motor control module 1412 operates the motor driver module 1414 and/or motor 1407 to achieve the commanded dosage, the motor control module 1412 ceases operating the motor driver module 1414 and/or motor 1407 until a subsequent dosage command is received. In this regard, the motor driver module 1414 and the motor 1407 enter an idle state during which the motor driver module 1414 effectively disconnects or isolates the stator windings of the motor 1407 from the energy source 1403. In other words, current does not flow from the energy source 1403 through the stator windings of the motor 1407 when the motor 1407 is idle, and thus, the motor 1407 does not consume power from the energy source 1403 in the idle state, thereby improving efficiency.

Depending on the embodiment, the motor control module 1412 may be implemented or realized with a general-purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 1412 includes or otherwise accesses a data storage element or memory, including any sort of random access memory (RAM), read only memory (ROM), flash memory, registers, hard disks, removable disks, magnetic or optical mass storage, or any other short or long-term storage media or other non-transitory computer-readable medium, which is capable of storing programming instructions for execution by the motor control module 1412. The computer-executable programming instructions, when read and executed by the motor control module 1412, cause the motor control module 1412 to perform or otherwise support the tasks, operations, functions, and processes described herein.

It should be appreciated that FIG. 14 is a simplified representation of the infusion device 1402 for purposes of explanation and is not intended to limit the subject matter described herein in any way. In this regard, depending on the embodiment, some features and/or functionality of the sensing arrangement 1404 may be implemented by or otherwise integrated into the pump control system 1420, or vice versa. Similarly, in practice, the features and/or functionality of the motor control module 1412 may be implemented by or otherwise integrated into the pump control system 1420, or vice versa. Furthermore, the features and/or functionality of the pump control system 1420 may be implemented by control electronics 1124 located in the fluid infusion device 1100, while in alternative embodiments, the pump control system 1420 may be implemented by a remote computing device that is physically distinct and/or separate from the infusion device 1402, such as, for example, the CCD 1006 or the computing device 1008.

Figure 15:
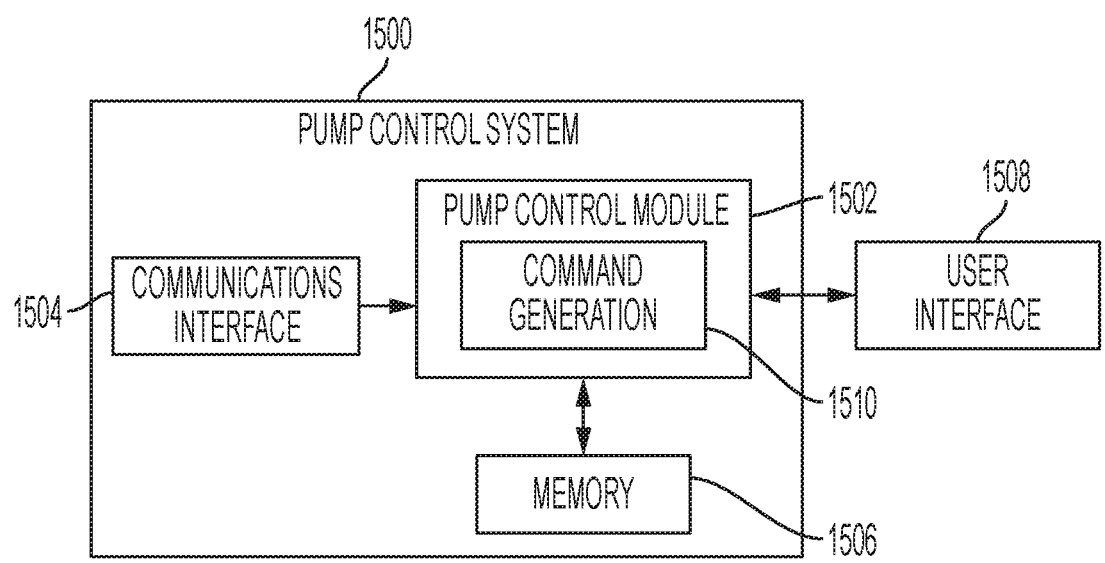
FIG. 15 is a block diagram of an exemplary pump control system suitable for use in the control system of FIG. 14.

FIG. 15 depicts an exemplary embodiment of a pump control system 1500 suitable for use as the pump control system 1420 in FIG. 14 in accordance with one or more embodiments. The illustrated pump control system 1500 includes, without limitation, a pump control module 1502, a communications interface 1504, and a data storage element (or memory) 1506. The pump control module 1502 is coupled to the communications interface 1504 and the memory 1506, and the pump control module 1502 is suitably configured to support the operations, tasks, and/or processes described herein. In exemplary embodiments, the pump control module 1502 is also coupled to one or more user interface elements 1508 (e.g., user interface 1130, 1440) for receiving user input and providing notifications, alerts, or other therapy information to the user. Although FIG. 15 depicts the user interface element 1508 as being separate from the pump control system 1500, in various alternative embodiments, the user interface element 1508 may be integrated with the pump control system 1500 (e.g., as part of the infusion device 1100, 1402), the sensing arrangement 1404 or another element of an infusion system 1000 (e.g., the computer 1008 or CCD 1006).

Referring to FIG. 15 and with reference to FIG. 14, the communications interface 1504 generally represents the hardware, circuitry, logic, firmware and/or other components of the pump control system 1500 that are coupled to the pump control module 1502 and configured to support communications between the pump control system 1500 and the sensing arrangement 1404. In this regard, the communications interface 1504 may include or otherwise be coupled to one or more transceiver modules capable of supporting wireless communications between the pump control system 1420, 1500 and the sensing arrangement 1404 or another electronic device in an infusion system 1000 or a patient management system. For example, the communications interface 1504 may be utilized to receive sensor measurement values or other measurement data from a sensing arrangement 1004, 1404 as well as upload such sensor measurement values to a server or other computing device for purposes of generating the GUI displays described herein. In other embodiments, the communications interface 1504 may be configured to support wired communications to/from the sensing arrangement 1404.

The pump control module 1502 generally represents the hardware, circuitry, logic, firmware and/or other component of the pump control system 1500 that is coupled to the communications interface 1504 and configured to determine dosage commands for operating the motor 1407 to deliver fluid to the body 1401 based on data received from the sensing arrangement 1404 and perform various additional tasks, operations, functions and/or operations described herein. For example, in exemplary embodiments, pump control module 1502 implements or otherwise executes a command generation application 1510 that supports one or more autonomous operating modes and calculates or otherwise determines dosage commands for operating the motor 1407 of the infusion device 1402 in an autonomous operating mode based at least in part on a current measurement value for a condition in the body 1401 of the user. For example, in a closed-loop operating mode, the command generation application 1510 may determine a dosage command for operating the motor 1407 to deliver insulin to the body 1401 of the user based at least in part on the current glucose measurement value most recently received from the sensing arrangement 1404 to regulate the user's blood glucose level to a target reference glucose value. Additionally, the command generation application 1010 may generate dosage commands for boluses that are manually-initiated or otherwise instructed by a user via a user interface element 1508.

Still referring to FIG. 15, depending on the embodiment, the pump control module 1502 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 1502, or in any practical combination thereof. In exemplary embodiments, the pump control module 1502 includes or otherwise accesses the data storage element or memory 1506, which may be realized using any sort of non-transitory computer-readable medium capable of storing programming instructions for execution by the pump control module 1502. The computer-executable programming instructions, when read and executed by the pump control module 1502, cause the pump control module 1502 to implement or otherwise generate the command generation application 1510 and perform the tasks, operations, functions, and processes described in greater detail below.

It should be understood that FIG. 15 is a simplified representation of a pump control system 1500 for purposes of explanation and is not intended to limit the subject matter described herein in any way. For example, in some embodiments, the features and/or functionality of the motor control module 1412 may be implemented by or otherwise integrated into the pump control system 1500 and/or the pump control module 1502, for example, by the command generation application 1510 converting the dosage command into a corresponding motor command, in which case, the separate motor control module 1412 may be absent from an embodiment of the infusion device 1402.

Figure 16:
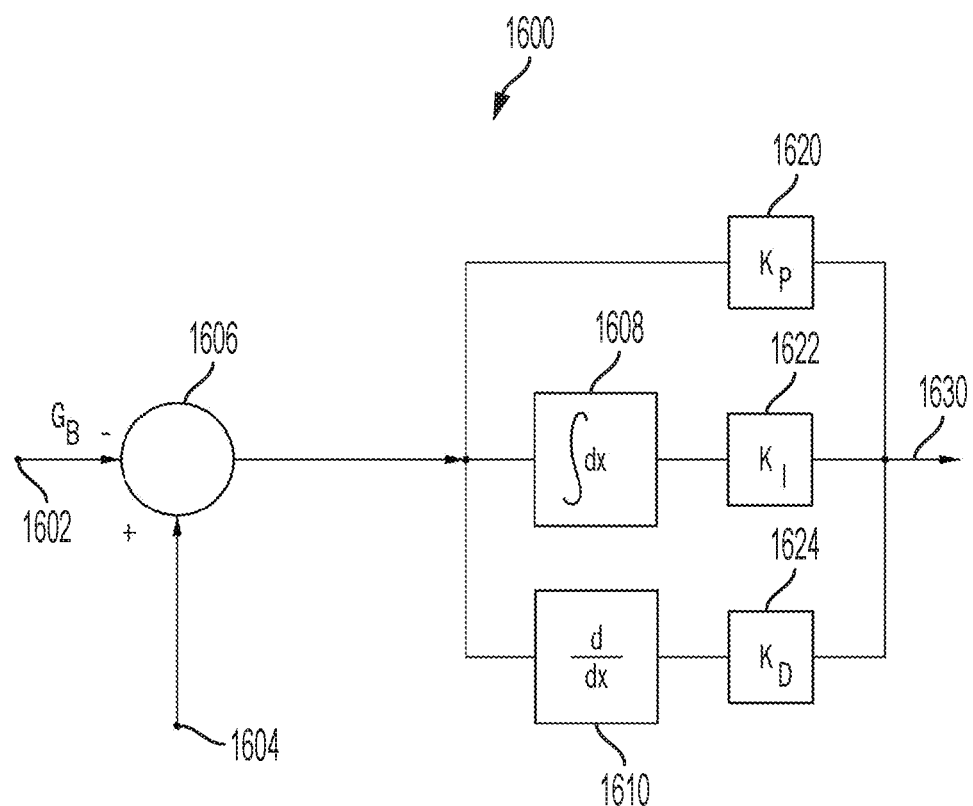
FIG. 16 is a block diagram of a closed-loop control system that may be implemented or otherwise supported by the pump control system in the fluid infusion device of FIG. 14 in one or more exemplary embodiments.

FIG. 16 depicts an exemplary closed-loop control system 1600 that may be implemented by a pump control system 1420, 1500 to provide a closed-loop operating mode that autonomously regulates a condition in the body of a user to a reference (or target) value. It should be appreciated that FIG. 16 is a simplified representation of the control system 1600 for purposes of explanation and is not intended to limit the subject matter described herein in any way.

In exemplary embodiments, the control system 1600 receives or otherwise obtains a target glucose value at input 1602. In some embodiments, the target glucose value may be stored or otherwise maintained by the infusion device 1402 (e.g., in memory 1506), however, in some alternative embodiments, the target value may be received from an external component (e.g., CCD 1006 and/or computer 1008). In one or more embodiments, the target glucose value may be dynamically calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 1600 also receives or otherwise obtains a current glucose measurement value (e.g., the most recently obtained sensor glucose value) from the sensing arrangement 1404 at input 1604. The illustrated control system 1600 implements or otherwise provides proportional-integral-derivative (PID) control to determine or otherwise generate delivery commands for operating the motor 1407 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 1602 and the measured glucose level at input 1604 to generate or otherwise determine a dosage (or delivery) command provided at output 1630. Based on that delivery command, the motor control module 1412 operates the motor 1407 to deliver insulin to the body of the user to influence the user's glucose level, and thereby reduce the difference between a subsequently measured glucose level and the target glucose level.

The illustrated control system 1600 includes or otherwise implements a summation block 1606 configured to determine a difference between the target value obtained at input 1602 and the measured value obtained from the sensing arrangement 1404 at input 1604, for example, by subtracting the target value from the measured value. The output of the summation block 1606 represents the difference between the measured and target values, which is then provided to each of a proportional term path, an integral term path, and a derivative term path. The proportional term path includes a gain block 1620 that multiplies the difference by a proportional gain coefficient, $K_P$, to obtain the proportional term. The integral term path includes an integration block 1608 that integrates the difference and a gain block 1622 that multiplies the integrated difference by an integral gain coefficient, $K_I$, to obtain the integral term. The derivative term path includes a derivative block 1610 that determines the derivative of the difference and a gain block 1624 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 1630.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 1402. The PID gain coefficients may be maintained by the memory 1506 accessible to the pump control module 1502. In this regard, the memory 1506 may include a plurality of registers associated with the control parameters for the PID control. For example, a first parameter register may store the target glucose value and be accessed by or otherwise coupled to the summation block 1606 at input 1602, and similarly, a second parameter register accessed by the proportional gain block 1620 may store the proportional gain coefficient, a third parameter register accessed by the integration gain block 1622 may store the integration gain coefficient, and a fourth parameter register accessed by the derivative gain block 1624 may store the derivative gain coefficient.

For the sake of brevity, conventional techniques related to glucose sensing and/or monitoring, bolusing, closed-loop glucose control, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of monitoring a plurality of patients, the method comprising:
    obtaining, by a server, measurement data of a physiological condition for the plurality of patients from a database, wherein respective measurement data associated with a respective patient of the plurality of patients was obtained from a respective medical device associated with the respective patient;
    obtaining, by the server, one or more prioritization rules from the database;
    generating, by the server, a prioritized list of the plurality of patients based on the measurement data in accordance with the one or more prioritization rules;
    providing, by the server, a dashboard graphical user interface (GUI) display on a client device coupled to a network, wherein the dashboard GUI display includes a patient list region comprising the prioritized list, wherein:
        the patient list region comprises a patient identification column, a patient status column, and a plurality of rows corresponding to the plurality of patients;
        each row of the plurality of rows is associated with a respective patient of the plurality of patients and includes a graphical representation of respective identification information associated with the respective patient in the patient identification column of the respective row and a graphical representation of a respective value for a metric indicative of a current state of the physiological condition of the respective patient in the patient status column of the respective row;
        for each row of the plurality of rows, the respective value for the metric indicative of the current state of the physiological condition of the respective patient in the patient status column of the respective row is determined based at least in part on the respective measurement data associated with the respective patient obtained from the database; and
        each row of the plurality of rows is ordered within the patient list region based at least in part on the respective value for the metric indicative of the current state of the physiological condition of the respective patient in accordance with the one or more prioritization rules;
    receiving, by the server from the network, updated measurement data of the physiological condition for one or more of the plurality of patients obtained from the respective one or more medical devices associated with the one or more of the plurality of patients;
    dynamically updating, for each patient of the one or more of the plurality of patients, the respective value for the metric indicative of the current state of the physiological condition of the respective patient based at least in part on a respective subset of the updated measurement data associated with the respective patient;
    identifying a first patient of the one or more of the plurality of patients exhibiting a prioritizable event based on the respective subset of the updated measurement data of the physiological condition for the first patient, wherein:
  the prioritizable event comprises a user-defined adverse event, and
  identifying the first patient exhibiting the prioritizable event comprises identifying when measurement values of the physiological condition for the first patient satisfy a user-defined threshold value for a user-defined monitoring period value associated with the prioritizable event based on an updated measurement value of the physiological condition for the first patient; and
dynamically updating, by the server, the patient list region of the dashboard GUI display at the client device in response to the updated measurement data to reflect an updated prioritized list of the plurality of patients, wherein:
  the first patient is dynamically reordered within the updated prioritized list in accordance with the one or more prioritization rules to be ranked ahead of at least one of the plurality of patients in response to the prioritizable event; and
  at least one of the plurality of patients is dynamically automatically reordered within the updated prioritized list below the first patient in accordance with the one or more prioritization rules in response to dynamically updating the respective value for the metric indicative of the current state of the physiological condition of the respective patient of the one or more of the plurality of patients in response to the updated measurement data.

2. The method of claim 1, further comprising determining a time in range value for each patient of the plurality of patients based at least in part on the respective subset of the measurement data associated with the respective patient, wherein secondarily ordering each respective patient of the plurality of patients based on the respective value for the metric indicative of the current state of the physiological condition of the respective patient comprises ordering at least some of the plurality of patients in the prioritized list in ascending order according to the respective time in range values.

3. The method of claim 1, wherein identifying the prioritizable event comprises detecting, by the server, an adverse event associated with the first patient of the plurality of patients in response to an updated measurement of the physiological condition associated with the first patient, wherein:
  the first patient is reprioritized in the updated prioritized list based on the adverse event in accordance with the one or more prioritization rules.

4. The method of claim 3, further comprising dynamically updating, by the server, a graphical indication of a status of the physiological condition of the first patient in response to detecting the adverse event, wherein the dashboard GUI display includes the graphical indication of the status of the physiological condition of the first patient in a row associated with the first patient.

5. The method of claim 3, further comprising:
  determining, by the server, a reason associated with reprioritization of the first patient in response to detecting the adverse event; and
  providing, by the server, a graphical indication of the reason on the dashboard GUI display in a row associated with the first patient within the patient list region.

6. The method of claim 3, further comprising:
  obtaining, by the server, electronic medical records data associated with the first patient from the database; and
  providing, by the server, a graphical representation of the electronic medical records data on the dashboard GUI display in a row associated with the first patient within the patient list region.

7. The method of claim 3, further comprising automatically generating, by the server, a message to the first patient in response to selection of a graphical user interface element on the dashboard GUI display in a row associated with the first patient within the patient list region.

8. The method of claim 3, further comprising automatically generating, by the server, a report GUI display corresponding to the first patient in response to selection of a graphical user interface element on the dashboard GUI display in a row associated with the first patient within the patient list region.

9. The method of claim 1, wherein the first patient is dynamically reordered within the updated prioritized list in accordance with a priority assigned to the user-defined adverse event.

10. The method of claim 1, further comprising:
  automatically determining a recommended therapeutic modification for the first patient based on historical data associated with the first patient, wherein the historical data includes at least one of historical measurement data and historical event log data; and
  automatically generating a selectable GUI element for providing the recommended therapeutic modification to a device associated with the first patient.

11. A system comprising a display device having rendered thereon a patient monitoring dashboard graphical user interface (GUI) display for concurrently monitoring a plurality of patients, the patient monitoring dashboard GUI display comprising a patient list region comprising a patient identification column, a patient status column, and a plurality of rows corresponding to the plurality of patients, wherein:
  each row of the plurality of rows is associated with a respective patient of the plurality of patients and includes a graphical representation of respective identification information associated with the respective patient in the patient identification column of the respective row and a graphical representation of a respective value for a metric indicative of a current state of a physiological condition of the respective patient in the patient status column of the respective row;
  for each row of the plurality of rows, the respective value for the metric indicative of the current state of the physiological condition of the respective patient in the patient status column of the respective row is determined based at least in part on respective measurement data associated with the respective patient obtained from a database;
  each row of the plurality of rows is ordered within the patient list region based at least in part on the respective value for the metric indicative of the current state of the physiological condition of the respective patient in accordance with one or more prioritization rules; and
  the patient list region is dynamically updated by dynamically reordering one or more rows of the plurality of rows within the patient list region in accordance with the one or more prioritization rules in response to dynamically updating the respective value for the metric indicative of the current state of the physiological condition for one or more of the plurality of patients in response to updated measurement data of the physiological condition for the one or more of the plurality of patients associated with the one or more rows, wherein:

a first patient of the one or more of the plurality of patients identified as exhibiting a prioritizable event based on a respective subset of the updated measurement data of the physiological condition for the first patient is dynamically reordered within the patient list region in accordance with the one or more prioritization rules to be ranked ahead of at least one of the one or more of the plurality of patients in response to the prioritizable event;

the prioritizable event comprises a user-defined adverse event;

the first patient exhibiting the prioritizable event is identified by identifying when measurement values of the physiological condition for the first patient satisfy a user-defined threshold value for a user-defined monitoring period value associated with the prioritizable event based on an updated measurement value of the physiological condition for the first patient; and the at least one of the one or more of the plurality of patients is automatically reordered within the patient list region below the first patient.

12. The system of claim 11, wherein for each row of the plurality of rows, the respective value for the metric indicative of the current state of the physiological condition of the respective patient in the patient status column of the respective row is dynamically determined in real-time in response to updates to the respective measurement data associated with the respective patient.

13. The system of claim 11, wherein each row of the plurality of rows includes at least one graphical user interface element that is selectable to initiate communication with the respective patient associated with the respective row.

14. The system of claim 11, wherein each row of the plurality of rows includes a graphical user interface element that is selectable to initiate presentation of a report graphical user interface display associated with the respective patient associated with the respective row.

15. The system of claim 11, wherein:

a visually distinguishable characteristic of the graphical representation of the respective value for the metric indicative of the current state of the physiological condition of the respective patient in the patient status column of a first row of the plurality of rows is influenced by an adverse event associated with the respective patient;

the adverse event is detected based at least in part on the respective measurement data associated with the respective patient associated with the first row; and a rank of the first row within the patient list region is influenced by the adverse event.

16. The system of claim 11, wherein the one or more prioritization rules are associated with a user of a client device that is authenticated by a remote server providing the patient monitoring dashboard GUI display on the display device associated with the client device, wherein the client device is communicatively coupled to the remote server over a communications network.

17. A system comprising:

a database to maintain one or more prioritization rules associated with a user of the client device and to maintain measurement data for a physiological condition of a plurality of patients, wherein respective measurement data associated with a respective patient of the plurality of patients is obtained from a respective medical device associated with the respective patient; and a server coupled to the database to obtain the measurement data for the plurality of patients from the database, obtain the one or more prioritization rules from the database, generate a prioritized list of the plurality of patients based on the measurement data in accordance with the one or more prioritization rules, provide a patient monitoring dashboard graphical user interface (GUI) display including patient list region comprising a graphical representation of the prioritized list on a client device coupled to the server over a communications network, and dynamically update the patient list region of the dashboard GUI display at the client device in response to receiving updated measurement data of the physiological condition for one or more of the plurality of patients obtained from the respective one or more medical devices associated with the one or more of the plurality of patients to reflect an updated prioritized list of the plurality of patients, wherein at least one of the plurality of patients is dynamically reordered within the updated prioritized list in accordance with the one or more prioritization rules in response to the updated measurement data, wherein:

the patient list region comprises a patient identification column, a patient status column, and a plurality of rows corresponding to the plurality of patients;

each row of the plurality of rows is associated with a respective patient of the plurality of patients and includes a graphical representation of respective identification information associated with the respective patient in the patient identification column of the respective row and a graphical representation of a respective value for a metric indicative of a current state of a physiological condition of the respective patient in the patient status column of the respective row;

for each row of the plurality of rows, the respective value for the metric indicative of the current state of the physiological condition of the respective patient in the patient status column of the respective row is determined based at least in part on respective measurement data associated with the respective patient obtained from the database;

each row of the plurality of rows is ordered within the patient list region based at least in part on the respective value for the metric indicative of the current state of the physiological condition of the respective patient in accordance with one or more prioritization rules; and the patient list region is dynamically updated by dynamically reordering a first row of the plurality of rows within the patient list region associated with a first patient identified as exhibiting a prioritizable event based on a respective subset of the updated measurement data of the physiological condition for the first patient in response to the prioritizable event in accordance with the one or more prioritization rules to be ranked ahead of one or more rows of the plurality of rows within the patient list region dynamically reordered below the first row in accordance with the one or more prioritization rules in response to dynamically updating the respective value for the metric indicative of the current state of the physiological condition for one or more of the plurality of patients in response to the updated measurement data of the physiological condition for the one or more of the plurality of patients associated with the one or more rows, wherein:
the prioritizable event comprises a user-defined adverse event, and
the first patient exhibiting the prioritizable event is identified by identifying when measurement values of the physiological condition for the first patient satisfy a user-defined threshold value for a user-defined monitoring period value associated with the prioritizable event based on an updated measurement value of the physiological condition for the first patient.

* * * * *